United States Patent
Maloney, Jr. et al.

[11] Patent Number: 5,900,142
[45] Date of Patent: *May 4, 1999

[54] MASS AND THERMAL TRANSFER MEANS FOR USE IN HEART LUNG MACHINES, DIALYZERS, AND OTHER APPLICATIONS

[76] Inventors: James V. Maloney, Jr., 139 Saltair, Los Angeles, Calif. 90049; Gerald D. Buckberg, 10833 Le Conte Ave., Room B2-375, Los Angeles, Calif. 90024

[*] Notice: This patent is subject to a terminal disclaimer.

[21] Appl. No.: 08/940,922

[22] Filed: Sep. 30, 1997

Related U.S. Application Data

[63] Continuation of application No. 08/434,458, May 3, 1995, Pat. No. 5,830,370, which is a continuation of application No. 07/924,183, Aug. 3, 1992, abandoned.

[51] Int. Cl.$^6$ .............................. B01B 33/00; B01B 35/18
[52] U.S. Cl. ............... 210/179; 210/321.63; 210/323.67; 210/321.68; 210/321.8; 210/321.88; 210/324; 210/330; 210/332; 422/46; 422/48
[58] Field of Search ......................... 210/321.63, 321.67, 210/321.68, 321.89, 321.87, 321.88, 321.79, 321.8, 223, 330, 695, 332, 780, 334, 781, 782, 175, 179; 422/46, 48

[56] References Cited

U.S. PATENT DOCUMENTS

| | | |
|---|---|---|
| 3,352,422 | 11/1967 | Heden . |
| 4,033,724 | 7/1977 | Tamiya . |
| 4,312,757 | 1/1982 | Brumfield . |
| 4,911,846 | 3/1990 | Akasu et al. . |
| 5,002,890 | 3/1991 | Morrison . |
| 5,011,469 | 4/1991 | Buckgerg NFPA . |
| 5,034,135 | 7/1991 | Fischel . |
| 5,143,630 | 9/1992 | Rolchigo . |
| 5,236,665 | 8/1993 | Mathewson et al. . |
| 5,263,924 | 11/1993 | Mathewson . |
| 5,270,005 | 12/1993 | Raible . |
| 5,271,743 | 12/1993 | Hattler . |
| 5,311,932 | 5/1994 | Sen et al. . |

OTHER PUBLICATIONS

One page sheet entitled "Cardiopulmonary Support (CPS) System Specifications" (not dated).

Brochure entitled "M–2000 Bi–Level Crossflow Membrane Oxygenator," by Shiley Incorporated (1984).

Brochure entitled "M–200 Membrane Oxygenator—Instructions for Use" by Shirley Incorporated (1983).

Brochure entitled "How We Wound Technology Into A High Performance Oxygenator" by Shiley Incorporated (1989).

Brochure entitled "This Is How We Top It" by Shiley Incorporated (1991).

Brochure entitled "Membrane Oxygenator" by Sarns Inc./3M (1988).

Japanese brochure entitled "Mera Excellung " by Mera (not dated).

Brochure entitled "Capiox® II, Hollow Fiber Oxygenator with Integrated Heat Exchanger" by Terumo Corporation (1984).

One page sheet entitled "Capiox™ II Standard Circuit Diagram" by Terumo Corporation (not dated).

Brochure entitled "Hi–Flex D700" by Electromedics, Inc. (not dated).

Brochure entitled "Univox, The Highly Integrated, Low Prime Membrane Oxygenator" by Baxter Healthcare Corporation (1990).

(List continued on next page.)

Primary Examiner—David A. Reifsnyder
Attorney, Agent, or Firm—Lyon & Lyon LLP

[57] ABSTRACT

The process, particularly useful in blood oxygenators, whereby a differential velocity between a fluid and a diffusing surface of hollow tubes by a rotating member such that the boundary layer is perturbed enhancing the coefficient of mass and thermal transfer. The differential velocity is achieved by rotating hollow tubes containing one fluid in a second fluid, or by apposing a rotating member to the surface of the stationary hollow tubes.

26 Claims, 15 Drawing Sheets

OTHER PUBLICATIONS

Brochure entitled "The Highest Performance Oxygenator Starts With the Lowest Prime" by Baxter Healthcare (1992).

Brochure entitled "You Told Us What You Wanted In An Oxygenator" by Extracorporeal, a Johnson & Johnson Company (1985).

Brochure entitled "Compendium of Scientific Information for the Maxima™ Hollow Fiber Oxygenator" by Johnson & Johnson Cardiovascular, a Johnson & Johnson Company (1985).

Reprint from vol. XVIII, Surgical Forum, American College of Surgeons, 1967 entitled "Boundary Layer Phenomenon in Membrane Oxygenators" by Illickal, M.D. et al.

Article from J. Cardiovasc. Surg. 24, 1983 entitled "Clinical Evaluation of the Interpulse Low Resistance Microporous Membrane Oxygenator" by karlson, M.D. et al.

Brochure entitled "Bio Pump® The Best Blood Delivery System for Bypass Perfusion" by Bio Medicus (1982).

One page sheet entitled "Bio Medicus® Portable Bypass Pack #7105" by Bio Medicus (not dated).

One page sheet entitled "Bio Medicus® Portable Bypass Pack #7106" by Bio Medicus (not dated).

Brochure entitled "Sarns™ Delphin™ Centrifugal System," by 3M Health Care (1990).

Brochure entitled "Sarns Delphin Centrifugal System, Technical Compendium," Sep. 1, 1991, by 3M Health Care.

Brochure entitled "Isoflow™ Centrifugal Pump Monograph," by Aries Medical (1990).

Brochure entitled "The Lifestream™ Centrifugal Pump System," by Aries Medical (not dated).

Article entitled "Respiratory System: External Respiration" by Fitz and Richards in *Medical Physics*, vol. III, Year Book Publishers, Chicago (1960).

Article entitled "Theory and Applications of Exchange of Inert Gas at Lungs and Tissue" by Kety, S.S., *Pharmacol. Rev.* 3:1 (1951).

Chapter III "Diffusion Rates in Turbulent Flow" pp. 139–184 and Chapter IV "Heat Transfer in Fluids" pp. 185–206 of *Physiochemical Hydrodynamics*, by Levich (English Translation from Russian), Prentice Hall, Englewood Cliffs, N.J. (1962).

Chapter I "Outline of Fluid Motion With Friction" pp. 5–23, Chapter II "Outline of Boundary Layer Theory" pp. 24–46, Chapter XVI "Origin of Turbulence I" pp. 449–488, Chapter XVII "Origin of Turbulence II" pp. 489–554, and Chapter XXI "Turbulent Boundary Layers at Zero Pressures Gradient; Flat Plate; Rotating Disk; Roughness" pp. 635–667 of *Boundary Layer Theory* by Schlichting (English Translation from German), McGraw Hill, New York (1979).

Chapter 3 "Rate Equations for Molecular Diffusion" pp. 54–100 of *Mass Transfer*, by Sherwood et al., McGraw Hill, New York (1975).

Book entitled *Flow and Heat Transfer in Rotating–Disc Systems, vol. 1—Rotor–Stator Systems*, by Owens and Rogers, J. Wiley & Sons, New York (1989).

Brochure entitled "Principles and Benefits of Membrane Oxygenation" by American Bentley (not dated).

Brochure entitled "Bentley Bos–CM40 and CM50 Capillary Membrane Oxygenators," by American Bentley (1985).

Product catalog by Scimed™ Surgical (1990).

Brochure entitled "Ultrox II Pediatric" by SciMed Life Systems, Inc. (1989).

Brochure entitled "A New Generation of the True Membrane™, the Only Membrane," by SciMed Life Systems, Inc. (not dated).

Brochure entitled "Scimed . . . The Best Lung Outside the Human Body . . . Is Now Practical to Use in All Procedures From 15 Minutes to 15 Days" by Scimed Life Systems, Inc. (1978).

Field Memorandum dated Aug. 1, 1981, by Scimed Life Systems, Inc., re: Customer Technical Bulletin/The Scimed Membrane Oxygenator System vs. Bubble Oxygenator Systems: Physiological and Mechanical Considerations.

Scimed Life Systems, Inc. Data and Instruction Manual, dated Aug. 1981.

Brochure entitled "Scimed's Integral Unit: Membrane Oxygenation Now Combined with Efficient Heat Exchange" by SciMed Life Systems Inc. (not dated).

Brochure entitled Scimed Pediatric Omnitherm™ Heat Exchanger Model P–7–14 by SciMed Life Systems Inc. (not dated).

Brochure entitled "Scimed Omnitherm™ Heat Exchanger" by SciMed Life Systems Inc. (not dated).

Brochure entitled "From Omnis, the LPM™/50 Membrane Oxygenator," by Omnis Surgical Inc. (1984).

Brochure entitled "COBE® CML" by COBE Laboratories, Inc. (1983).

Brochure entitled "COBE® CML Excel The Membrane Oxygenator Designed by the Specialists" by COBE Laboratories, Inc. (1988).

One page sheet by COBE Laboratories Inc. (1983).

Brochure entitled "What Makes This New Membrane Oxygenator So Advanced?" by Bard Cardiopulmonary Division (not dated).

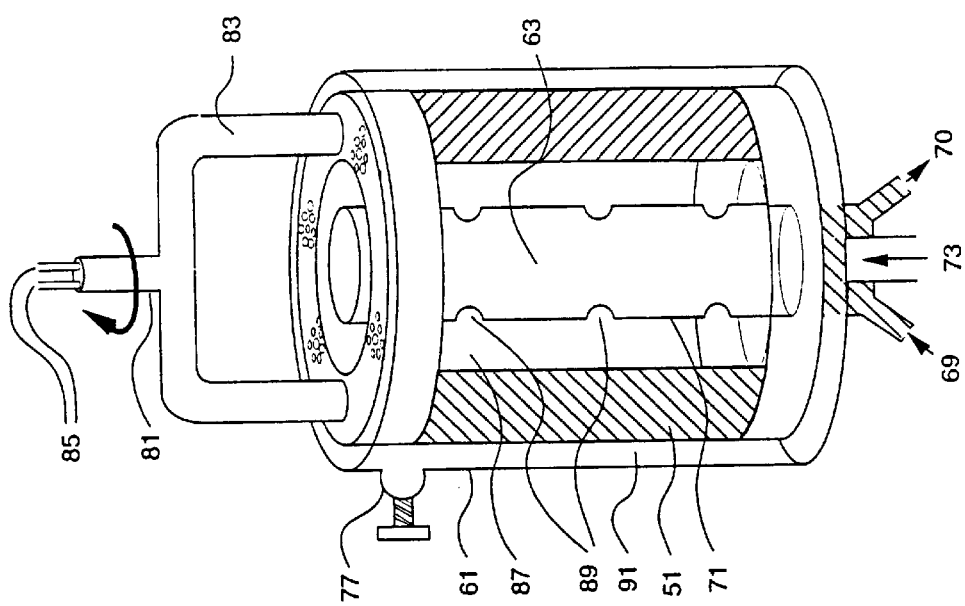
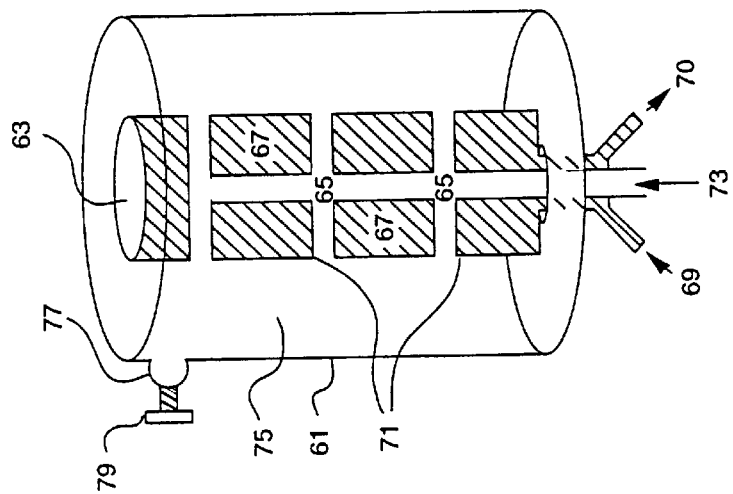
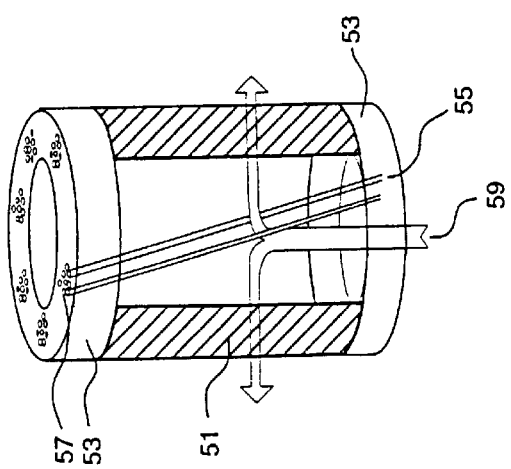

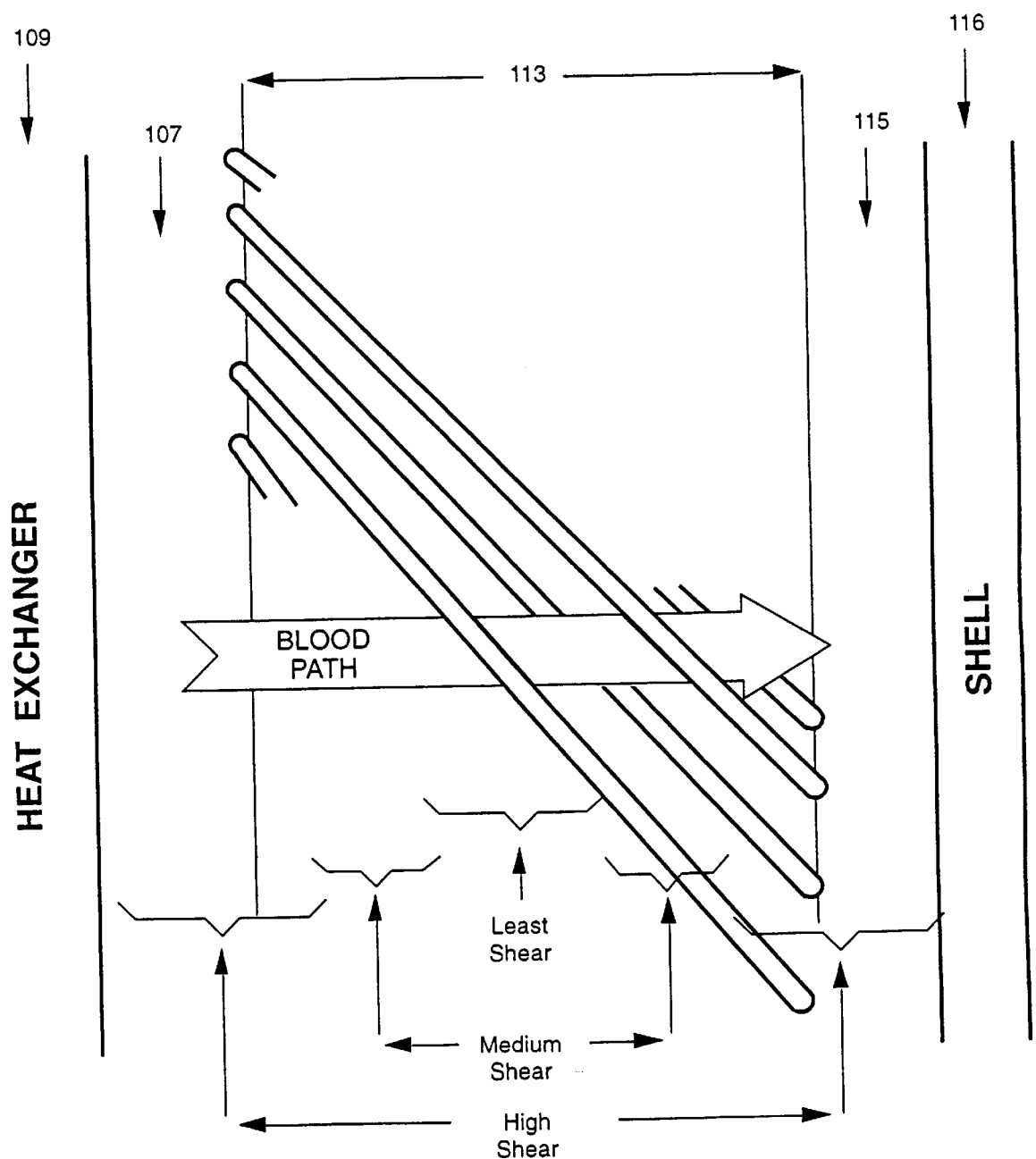

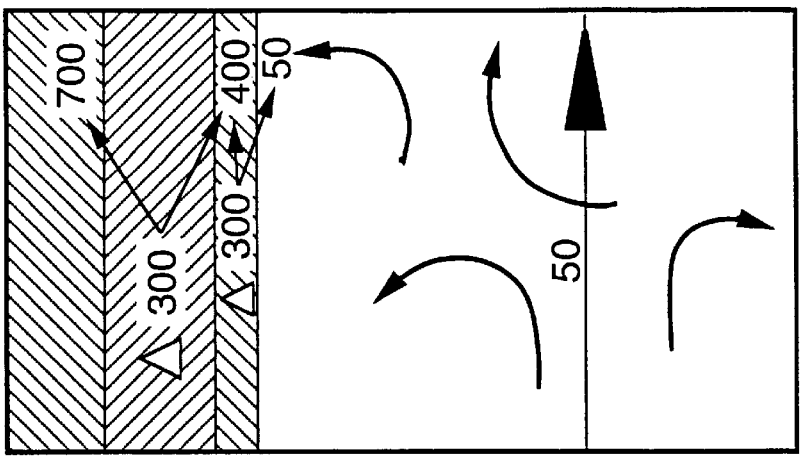
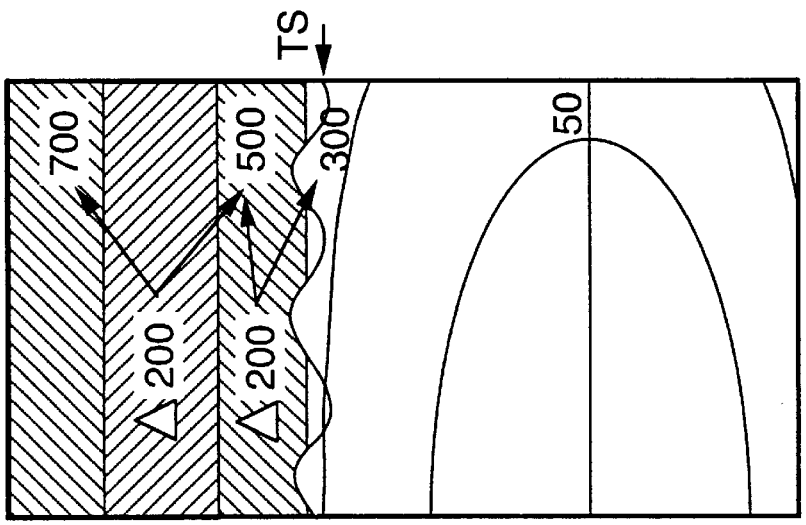
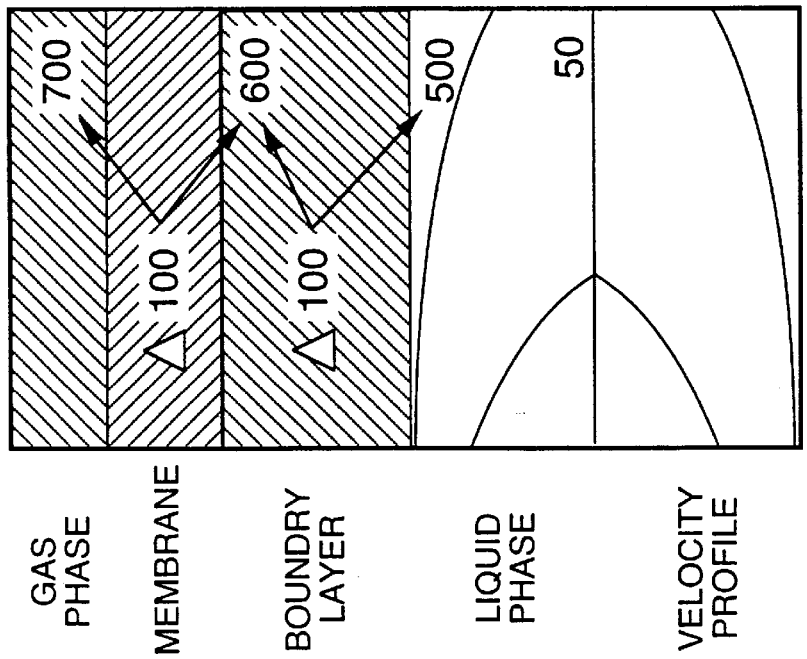

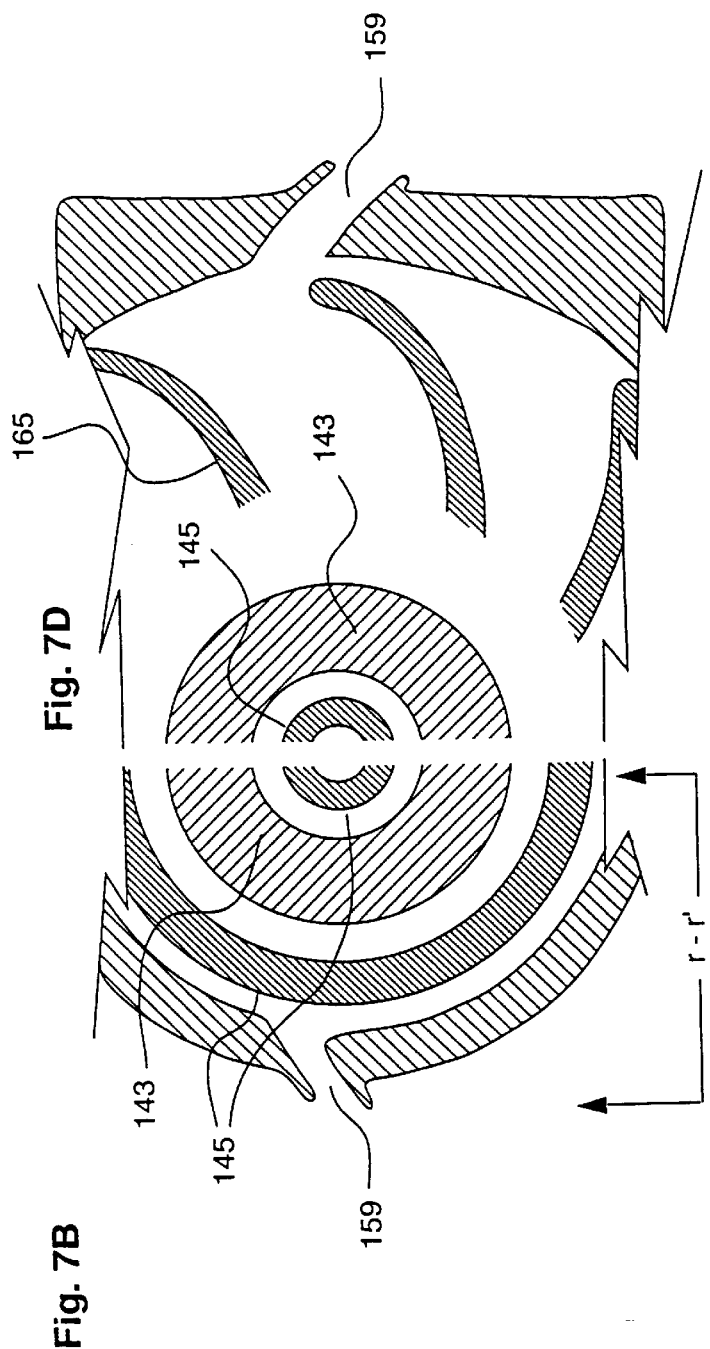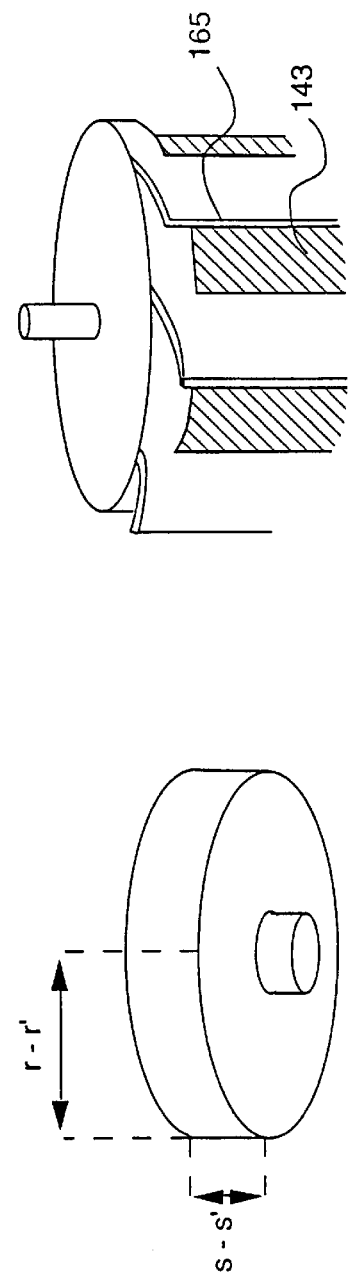
Fig. 7B
Fig. 7D
Fig. 7C
Fig. 7E

MASS AND THERMAL TRANSFER MEANS FOR USE IN HEART LUNG MACHINES, DIALYZERS, AND OTHER APPLICATIONS

This is a continuation of application Ser. No. 08/434,458, filed May 3, 1995 now U.S. Pat. No. 5,830,370, which is a continuation of application Ser. No. 07/924,183, filed Aug. 3, 1992 now abandoned.

BACKGROUND OF THE INVENTION

The field of invention is generally related to mass and thermal transfer in a manner that is particularly useful in blood oxygenators and other medical devices.

A brief history and present status of relevant technology is appropriate to understanding the subject invention with regard to medical applications. There has been a need to utilize principles of mass and heat transfer more effectively in, for example, oxygenators and dialyzers.

For example, heart-lung machines, which utilize oxygenators, are employed during surgery in the USA approximately 300,000 times per year. Renal dialysis is performed approximately 750,000 times per week on 250,000 people to sustain the life in the presence of kidney failure. These examples in medicine and a score of others in industry attest to the need for compact devices which permit the transfer of gases, solutes, liquids, and/or heat across metallic and synthetic surfaces. Especially in medical applications, efficiency (transfer rates per unit surface area, per unit volume, per unit flow, and per unit priming volume) is critically important because of limited flow rates and small working volumes characteristic of human physiology.

The typical heart-lung machine consists of a complex interlinkage of 4 to 6 separate components, including a pump, oxygenator, heat exchanger, flow meter, and dynamic reservoir; the components being connected together by plastic tubing through which blood and water flow (see FIG. 1). The disadvantages of the present heart-lung machines are several. They include an inordinately large priming volume. Priming volume refers to the amount of blood or blood substitute required to fill the device prior to use. It is important to reduce the priming volume to minimize the danger of AIDS and hepatitis. Economic costs of blood and fluid are also important reasons to reduce the priming volume of extracorporeal circuits. Normal adults can typically only tolerate the loss of 500 to 1,000 ml (milliliters) of blood during operation, but cannot sustain losing an additional 1,250 to 2,500 ml to prime the device. It is therefore common for patients undergoing open heart surgery to receive multiple transfusions of blood. The cost of filling the priming volume with a mixture of blood or blood substitutes can be as much as $1,000 (blood processing, saline solution, plasma, hydroxy ethyl starch cost between $40 and $330 for each 500 ml required).

Inefficient mass transfer of oxygen and carbon dioxide is also a problem in heart-lung machines. Membrane surface areas of 2 to 4 $M^2$ (square meters) are typically required, necessitating high expense and large priming volumes. The hundreds of thousands of commercial membrane oxygenators and heat exchangers used each year have oxygen transfer rates of 70–100 cc/$M^2$/min (cubic centimeters per square meter per minute) and heat transfer rates of 2 to 4 cals/$cm^2$/C.°/min (calories per square centimeter per degree centigrade per minute). These rates are essentially the same for all available commercial devices except for small variations achieved by induction of low levels of turbulence by alteration of flow paths. As will be explained, the efficiency of all current devices is limited by the boundary layer effect as it influences the operation of the Fick diffusion equation at the diffusion surface.

Yet another problem with heart-lung machines is the risk of air embolism from the reservoir. The dynamic (see below) blood reservoir is open to the atmosphere, thus requiring constant human monitoring to prevent massive air embolism. Moreover, the reservoir typically accounts for 500–1500 ml of total priming volume, and exposes blood protein to damage due to surface free energy at the air-fluid interface.

Another drawback is the operational complexity induced by multiple interdependent components connected by plastic tubing, as shown in FIG. 1.

Also of concern is the expense resulting from the cost of the 4 to 6 disposable components which comprise the heart-lung machine, which cost from $100 to $450 per item. Currently, practices typically cause the disposal of these items after each surgery.

Finally, expensive hardware is needed for monitoring the blood flow rate through the heart-lung machine system. Expensive electromagnetic or Doppler flow meters are used with centrifugal pumps.

Current devices for renal dialysis suffer analogous impediments. Limited mass transfer rates require that patients be attached to artificial kidneys for 4 hours three times per week to sustain life.

The above-mentioned disadvantages are only a fraction of the problems encountered by existing technology.

Over twenty (20) years ago, one of the subject inventors reported on the impediment to diffusion created by the boundary layer adjacent to the diffusing surface, Maloney, J. V., Brown, G. E., Van de Water, J. M., Lee, W. H., Pall, D. B. *Boundary Layer in Membrane Oxygenators,* 18 Surg. Forum 134–136 (1967). This 1967 work, like the efforts by many other investigators, failed to produce a practical device, in part due to the heat generated by intermolecular friction in the fluid which was detrimental to red blood cells. The flat surface, despite rotation, was so inefficient as a diffusion surface that the energy required produced more heat than was practical to dissipate. Accordingly, this work was deemed unsuccessful and was abandoned. The substitution of microporous hollow fibers for solid membranes a decade ago reduced from 4 to 2 $M^2$ the membrane surface area required in oxygenators. Otherwise, in the 25 years since the 1967 article, little has been done to further the technology. Commercial endeavor has been directed in the past 15 years to altering the flow path between hollow fibers in an attempt to induce turbulence and increase diffusion. The efforts have produced minor improvements in gas transport in the range of 10 percent. A similar lack of progress characterizes the current status of diffusion rates through wettable fibers in renal dialysis.

Accordingly, there has been need for an effective and practical means for improving mass transfer in compact diffusion devices. The subject invention achieves mass and heat transfer rates never before obtained.

SUMMARY OF THE INVENTION

The process of the invention perturbs the boundary layer by creating a differential velocity between fluid and a diffusing surface by rotational motion such that enhanced coefficient of mass and thermal transfer are obtained.

The process has wide applications in oxygenators, heart-lung machines, dialyzers, artificial kidneys, and other medical and industrial uses where efficient mass and thermal transfer must be achieved in a compact space with minimal priming volumes. Illustrative prototypes are described and their operation is shown to result in transfer rates many-fold greater than those currently achievable. The application of the process of the invention to existing products increases safety and produces savings in cost, complexity, surface area, and size. Of significant importance is the reduction of blood priming volumes in medical devices to a level which facilitates the performance of procedures without the use of blood or blood substitutes. The millions of hollow fiber oxygenators and dialyzers manufactured each year in the U.S. would achieve a substantial improvement in function by the application of this invention.

The rate-limited nature of the diffusion of solutes across artificial and biological membranes causes 250,000 people in the U.S. to spend 150,000,000 hours connected to artificial kidneys each year. Although the existence of the boundary layer is universally recognized, attempts to perturb it by creating curved flow paths in bundles of hollow fibers have produced insignificant benefit. Johnson and Johnson (Johnson & Johnson, Inc., Successors-in-Interest, Cardiopulmonary Products Division, Medtronic, Inc.) experimented with a vibrating membrane ("Shake-and-Bake") to perturb the boundary layer, but it has not found practical application. To the inventors' knowledge, the only previous use of rotary motion to perturb the boundary layer to enhance oxygen transfer through porous membranes is that described in the previously referenced 1967 publication by one of the inventors which, for reasons stated, failed and was abandoned.

Scores of publications and dozens of commercial products attest to the general recognition of the boundary layer as an impediment to efficient mass and thermal transfer in heart-lung machines and artificial kidneys. Yet, a billion dollar industry with substantial research and development budgets have failed to achieve the benefits this invention offers.

The components of all current pump-oxygenators and renal dialyzers includes a diffusing membrane, pump, heat exchanger, and flow meter. Yet, despite their use in millions of instances over three decades, it has not been appreciated that a single physical principle would allow each of the four components to be combined in a single unit with an improvement in form, function, economy, and safety. There exists a specific non-linear relationship among pressure drop across a centrifugal pump, RPM (rotations per minute) and flow rate under conditions of constant kinematic viscosity. The fact that to use this differential pressure as a measure of flow is a departure from conventional thinking is attested to by the production each year by competing manufacturers of hundreds of consoles and tens of thousands of centrifugal blood pumps in conjunction with Doppler and electromagnetic flow meters as, for example, in devices manufactured and/or distributed by Biomedicus/Medtronic, Centrimed/Sarnes, and Isoflow/St. Jude.

The invention utilizes the principle of increasing mass and heat transfer beyond levels currently achievable by employing hollow fiber technology, and applying shear stress to the boundary layer by means of a rotating system. Integral with the same principle, and contained within the same housing, the following objectives are met: (a) mass transfer coefficients not otherwise achievable; (b) heat exchange coefficients not otherwise achievable; (c) a pressure head generated by shear that incidentally serves as a pump; and (d) use of the differential pressure within the housing to serve as a flow meter. Indeed, there exists a plurality of embodiments, depending on the circumstances and objectives of the application.

The application of the best mode of the invention to heart-lung machines achieves at least the following benefits over current art:

(1) The fiber bundle is smaller and contains a fraction of the typical 2 to 4 $m^2$ membrane surface area, thus reducing the priming volume and expense;

(2) The heat exchange surface is a fraction of the area currently needed for extracorporeal circulation and adds no priming volume to the system;

(3) The energy imparted to the blood by the rotating member creates a pressure head, eliminates the need for the conventional pump, and avoids additional priming volume;

(4) The 4 to 6 typical components of a heart-lung machine are supplanted by a single embodiment;

(5) The differential pressure across the embodiment provides a simple measure of flow without increase in priming volume and with a substantial reduction in cost;

(6) The overall priming volume is a fraction of that necessary in current devices, reducing the possibility of blood-borne infection. Aspects of the claimed invention in combination with inventors' previously patented non-dynamic reservoir system (U.S. Pat. No. 5,011,469) reduces the usual priming volume of the machine from 1500 to 2500 ml to approximately 250 ml (exclusive of tubing to patient), eliminating the need for blood transfusion in most patients and minimizing it in others; and (7) Decreased risk of air embolism.

Analogous benefits would apply to: diffusion of liquids and solutes in the artificial kidney; thermal transfer in heat exchangers; and other devices requiring diffusion, pumping and flow measurement in a compact space.

BRIEF DESCRIPTION OF THE DRAWINGS

FIG. 1-B shows a mode of the subject invention which combines the 5 components and tubing from FIG. 1-A into a single unit having a low priming volume and the other benefits of the invention. Broken lines indicate a non-dynamic reservoir employed only in emergencies.

FIG. 2-A is a plan view, partially in cross-section, of a cylindrical bundle of non-wettable hollow microporous synthetic tubing (approximately 4,000 tubes, 0.4 $M^2$ surface area) which is used in the claimed blood oxygenator. Oxygen is passed through the microtubules while blood flows over the surface of the fibers. Commercially available hollow fiber oxygenators contain fibers in a similar conformation, although in some, the blood is within and gas outside the fibers.

FIG. 2-B is a plan view, partially in cross-section, of an outer shell and an inner central diffuser. The central diffuser, not only serves to distribute incoming blood evenly throughout the oxygenator, but includes an integral heat exchanger essential to heart-lung machines.

FIG. 2-C depicts an assembled device where a cylindrical annular fiber bundle is suspended by an armature between the central diffuser and the outer shell and rotated by a ducted shaft carrying oxygen to the fiber bundle, thus perturbing the interface boundary layer between blood and fiber.

FIG. 3-B is a magnified view through plane a'—a' in FIG. 3-A, illustrating the blood path from the central diffuser/heat exchanger and through the fiber bundles. It illustrates the relative magnitude of the shear rates as the fiber bundle rotates. Shear is greatest where the rotating fibers are in apposition to a stationary wall and least in the central portion of the fiber bundle where blood is accelerated to the same velocity as the moving fibers.

FIGS. 4A–4C are condensed and simplified illustrations of the manner in which increasing relative motion between the diffusing surface and the blood perturbs the boundary layer as the flow regime changes from laminar to turbulent. The imputed partial pressures of oxygen illustrate the change in diffusion gradients across the boundary layer and the membrane. Diffusion capacity is a function of these gradients (see Fick equation).

FIG. 7-B is a cross-section taken through plane i—i in FIG. 7-A showing dual rotating cylinders.

FIG. 7-C illustrates the proportional dimensions of the radius of the rotating cylinders to the length of the cylinders.

FIG. 7-D illustrates generally the same structure as FIG. 7-B except that the outer rotating cylindrical member is replaced by vanes 143 to improve pumping efficiency while still perturbing the outer boundary layer.

FIG. 7-E is a pictorial representation of the cross-section of FIG. 7-D.

DESCRIPTION OF PREFERRED EMBODIMENTS

Figure 1A:
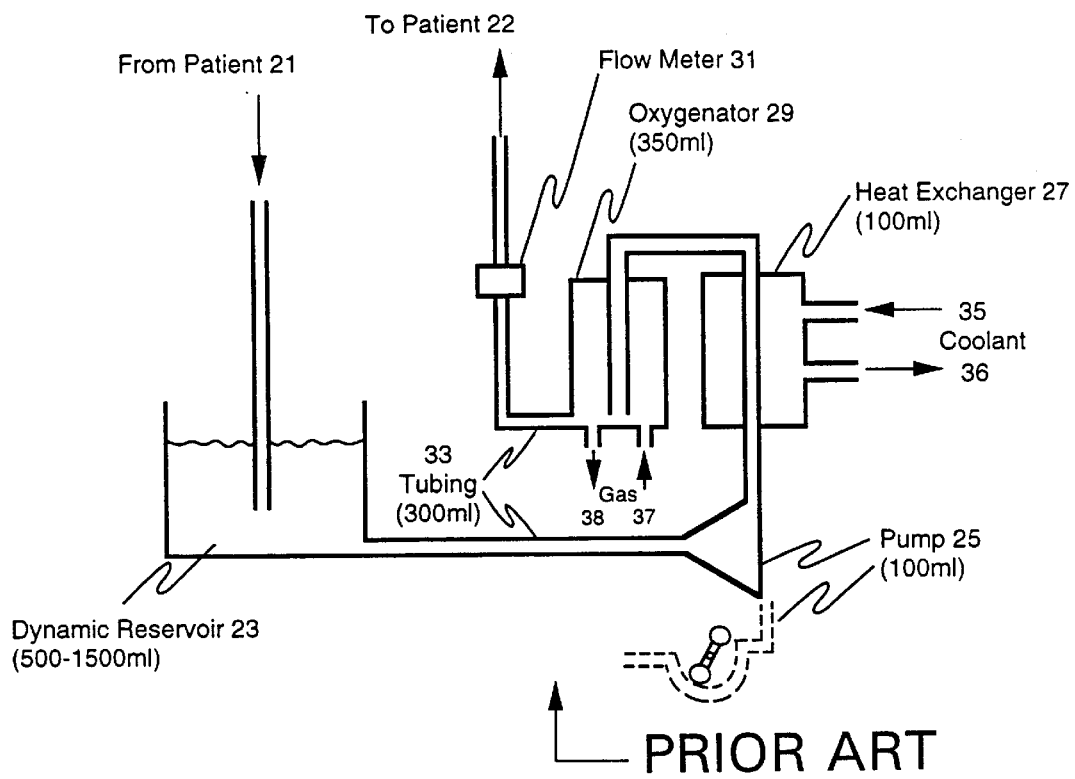
FIG. 1-A is a schematic illustration of currently available state of the art heart-lung machine with its characteristic multiple components: dynamic reservoir 23, pump 25, heat exchanger 27, oxygenator 29, flow meter 31, interconnected by tubing 33 and characterized by a large priming volume.
Figure 1B:
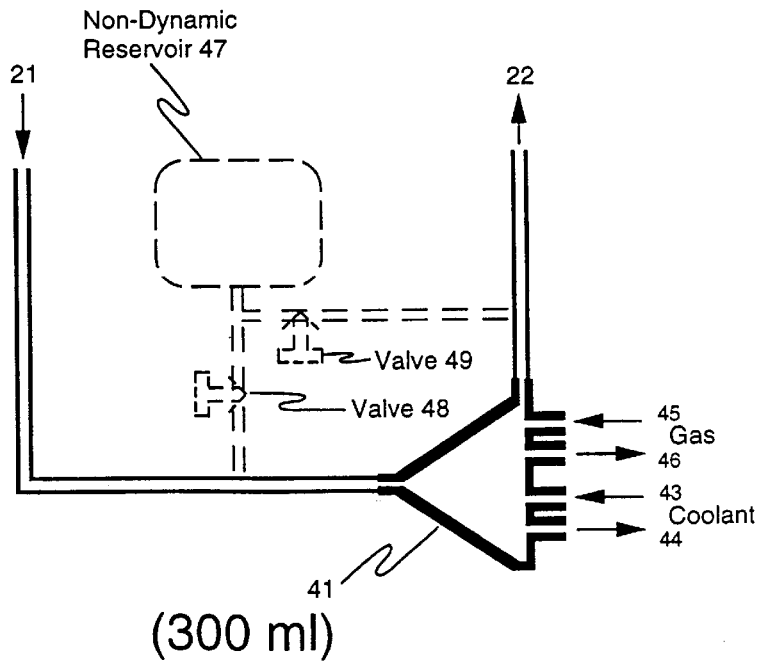

FIG. 1-A illustrates state of the art extracorporeal circulation as utilized in a conventional heart-lung machine. The current heart-lung machine consist of 4 to 6 separate components including a pump 25, oxygenator 29, heat exchanger 27, flow meter 31, and dynamic reservoir 23; the components being connected together by plastic tubing 33 through which blood and water flow. Venous blood comes from the patient 21 into a rigid open reservoir 23 in series with the circulating (dynamic) blood reservoir. It is propelled serially by a centrifugal pump 25 (or displacement roller pump, broken lines) through a heat exchanger 27 and oxygenator 29, past a flow meter 31 (with centrifugal pumps), and back to the patient 22. While in the oxygenator 29, oxygen diffuses into the blood while carbon dioxide diffuses out. All the components are connected by plastic tubing 33.

Proceeding in more detail in the same order as FIG. 1-A, the dynamic reservoir 23 typically contains 500–1500 ml of blood. Pump 25 is typically a roller-type displacement pump (De Bakey); recently, centrifugal pumps are employed in approximately 100,000 patients per year because of putative safety advantages related to the prevention of gas macroembolism. One such pump is of the shear type (Biomedicus); two others are of the radial impeller type employing conventional vanes (Centrimed/Sarnes and Isoflow/St. Jude).

Still referring to FIG. 1-A, a heat exchanger or temperature controlling device 27 is used to produce the necessary changes in body temperature required for extracorporeal circulation. Coolant for heating or for cooling, enters the heat exchanger 27 via port 35 and exits via port 36. Initially, standard industrial counter-current shell-and-tube heat exchangers were employed. Many, but not all, manufacturers have subsequently integrated industrial type corrugated conduit or "radiator" type heat exchangers into the structure of the membrane oxygenator. Heat exchange rates of current devices are fairly satisfactory, but add undesirable priming volume.

Proceeding to the oxygenator 29, gas containing oxygen enters via port 37 and exits via port 38. The common press-and-plate membrane oxygenators and bubble diffusion oxygenators have been generally replaced by microporous tubule membrane oxygenators because of the morbidity and mortality caused by gas micro-emboli (bubble devices) and by the technical inconveniences of plate-and-press membrane oxygenators. Hollow fiber technology using microporous non-wettable polymers is widely used, but without the boundary layer perturbance mechanism as claimed in the subject invention.

While the large reserve volume in the open dynamic reservoir is not necessary when the machine is being used for circulatory support in the hospital ward (since there is no danger of sudden blood loss), it is essential in the operating room. The dynamic reservoir is open to the atmosphere, requires constant monitoring to prevent air embolism, and the blood proteins can become damaged by the surface free energy at the air-fluid interface.

The priming volume of components is illustrated. Priming involves 1,250 to 2,500 ml, which in most cases requires the use of blood, blood components, and/or blood substitutes such as isotonic saline, plasma, saline with human albumin, and hydroxy ethyl starch. The priming of the current machines and operative blood loss typically requires blood from exogenous sources.

FIG. 1-B schematically illustrates one mode of the invention whereby all of the previously mentioned separate components are combined into one device 41 which the inventors refer to as a "pumpgenator." Venous blood comes from the patient 21 into the pumpgenator 41, which consists of a single housing which employs a rotating member to perturb the boundary layer on a hollow fiber bundle. Within the pumpgenator 41 there is a heat exchanger with a heat exchange surface that is scraped by the rotating member. Coincidentally, the rotating member creates a pressure head within the device so that the need for a pump, heat exchanger, flow meter, and their related priming volumes are eliminated. Coolant enters the pumpgenator 41 through port 43 and exits via port 44. Gas containing oxygen enters the invention via port 45 and exits via port 46. The blood, after heat and oxygen transfer, can then return to the patient 22. The inventors' closed, flexible non-dynamic reservoir 47 (U.S. Pat. No. 5,011,469, Buckberg et al. peripheral cardiopulmonary bypass and coronary perfusion system) remains isolated by valves 48 and 49 and does not add to priming volume unless it is needed in an emergency in the case of catastrophic blood loss. Opening valve 48 transfers fluid (blood or blood substitute) at a rate of 0.2 to 10.0 LPM (liters per minute) into the patient. Opening valve 49 transfers patient blood from the body into the storage reservoir to be used later in the procedure. The total priming volume is approximately 250 ml, which makes it possible in most cases to avoid the use of exogenous blood.

FIGS. 2-A, 2-B, and 2-C illustrate schematically one of the principles of the invention specifically applicable to improved oxygenation of blood. FIG. 2-A shows a cylindrical bundle of hollow fibers (approximately 4,000 in number) employed as a diffusion surface. The fibers 51 are embedded in potting material 53 at each end of the cylinder. Gas for exchange, typically oxygen, enters individual fibers at the bottom 55 and exits the top 57 of the cylinder. Blood from the patient 59 is forced by pumping action to pass through the interstices between the hollow fibers and thus contacts the diffusing surface of the fibers. The fibers are made up of a microporous non-wettable diffusion membrane, which allows transfer of gas (oxygen) but not liquids (blood). A wettable semipermeable diffusion membrane would be substituted for the microporous non-wettable diffusion membrane in dialyzers to allow the transfer of liquids and crystalloids, but not cells and colloids. The packaging of the fibers into a bundle in FIG. 2-A is similar to that used in some commercial oxygenators.

FIG. 2-B shows the housing into which the cylinder of fiber bundles in 2-A is inserted as one aspect of the invention. The outer shell 61 of the apparatus surrounds a central diffuser 63 within which blood 65 and coolant 67 flow in separate channels. The coolant enters at 69, is constrained within the diffusing structure, is evenly disbursed, and circulates to contact the heat exchange surface 71 of the diffuser 63 and then exits from the central core at 70. Blood enters at input port 73, is ducted and distributed through the diffuser 63 to enter the space 75 between the diffuser 63 and the outer shell 61. Blood exits at tangential orifice 77 controlled by valve 79.

FIG. 2-C illustrates the insertion of the fiber bundle 51 into the housing (outer shell 61). The fiber bundle 51 has been modified by the attachment of a manifold (not shown) and a ducted rotor shaft 81 and armature 83 which carry gas 85 to and from the hollow fibers 51. The fiber bundle 51 is suspended by the armature 83 and ducted rotor shaft 81 in the space between the diffuser 63 and the outer shell 61. Blood enters port 73 and passes through diffuser 63 from which it enters inner blood space 87 through ports 89. Blood passes through fiber bundle 51 to enter outer blood space 91. Rotation of the fiber bundle 51 within the relatively viscous blood creates shear between the blood and the diffusing surface of the fiber bundle because of the apposition of the rotor to a stationary surface (diffuser 63 and shell 61). The rotational motion of the fiber bundle 51 also causes the perturbation of the boundary layer between the blood and the heat exchange surface 71, facilitating thermal transfer.

The rotation results in improved oxygenation and improved heat exchange. Perturbation of the boundary layer enhances thermal transfer at the heat exchange surface through the same mechanism by which mass transfer is enhanced in the oxygenator. Without additional "cost" (priming volume, energy, size, and blood trauma), rotary motion in the blood induced by the rotating fiber bundle 51 creates shear which enhances heat exchange. The need for a component heat exchanger and additional priming volume is eliminated.

Figure 13:
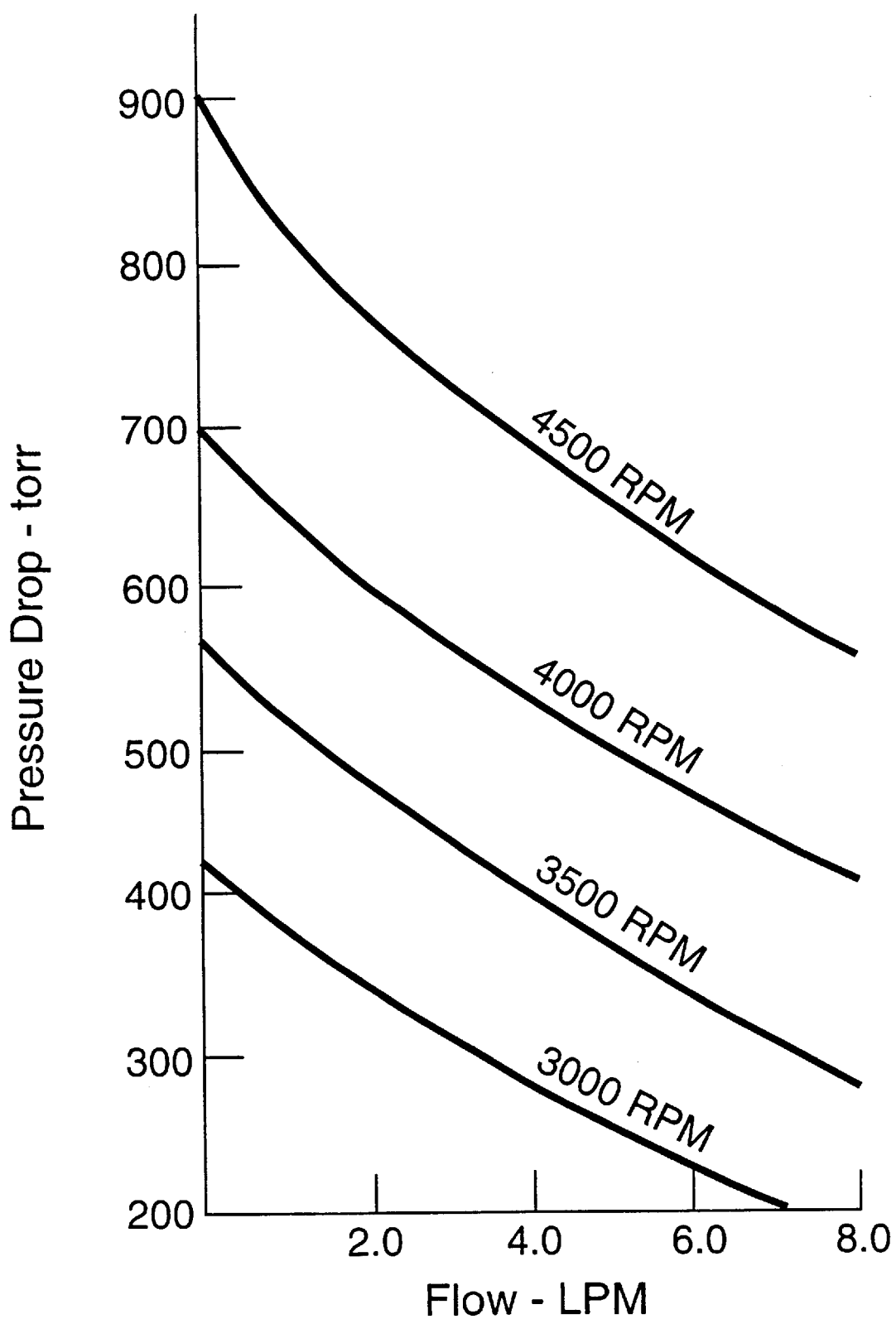
FIG. 13 is a the three dimensional plot illustrating the fixed relationships between the difference in pressure across the blood flow path and RPM in a prototype. Knowledge of the RPM and pressure provides a continuous indication of flow rate.

Another benefit of this aspect of the invention is that it eliminates the need for a separate pump. The rotary motion of the fiber bundle in the viscous blood creates hydrodynamic drag and generates a pressure head (Tesla effect). A variable gate valve 79 at blood outlet 77 controls the pressure head to allow the desired flow of blood from the shell to the patient. Another concomitant benefit of this process is its utilization to provide a flow meter function. In keeping with the Tesla effect and as illustrated in FIG. 13, with a specific rotation rate and fluid viscosity, there is a fixed, inverse, and non-linear relationship between flow rate and pressure drop across the apparatus. Thus, the conventional Doppler or electromagnetic flow meter may be supplanted by a simple measure of the differential pressure between points 73 and 77 in FIG. 2-C. Again, another physical component and expense are dispensed with.

In summary, the creation of shear on the surface of the fiber bundle and the differential motion between a fixed and rotating surface creates an oxygenator which exceeds the performance of any known conventional device. Without additional "costs", a need for separate heat exchanger or temperature controlling device is eliminated by the creation of diffusion surface with a coefficient of heat transfer which exceeds by several fold the performance of existing exchangers. Similarly, the need for a blood pump and a flow meter are eliminated by taking advantage of physical forces inherent in such a unique oxygenator and heat exchanger. This aspect of the inventive concept so illustrated in a "pumpgenator" applies to a broad range of compact devices for mass and thermal transfer. For example, the "pumpgenator" could be used for blood dialysis when the hollow fibers are made out of wettable semi-permeable material, and dialysis solution is used instead of oxygen containing gas.

Figure 3A:
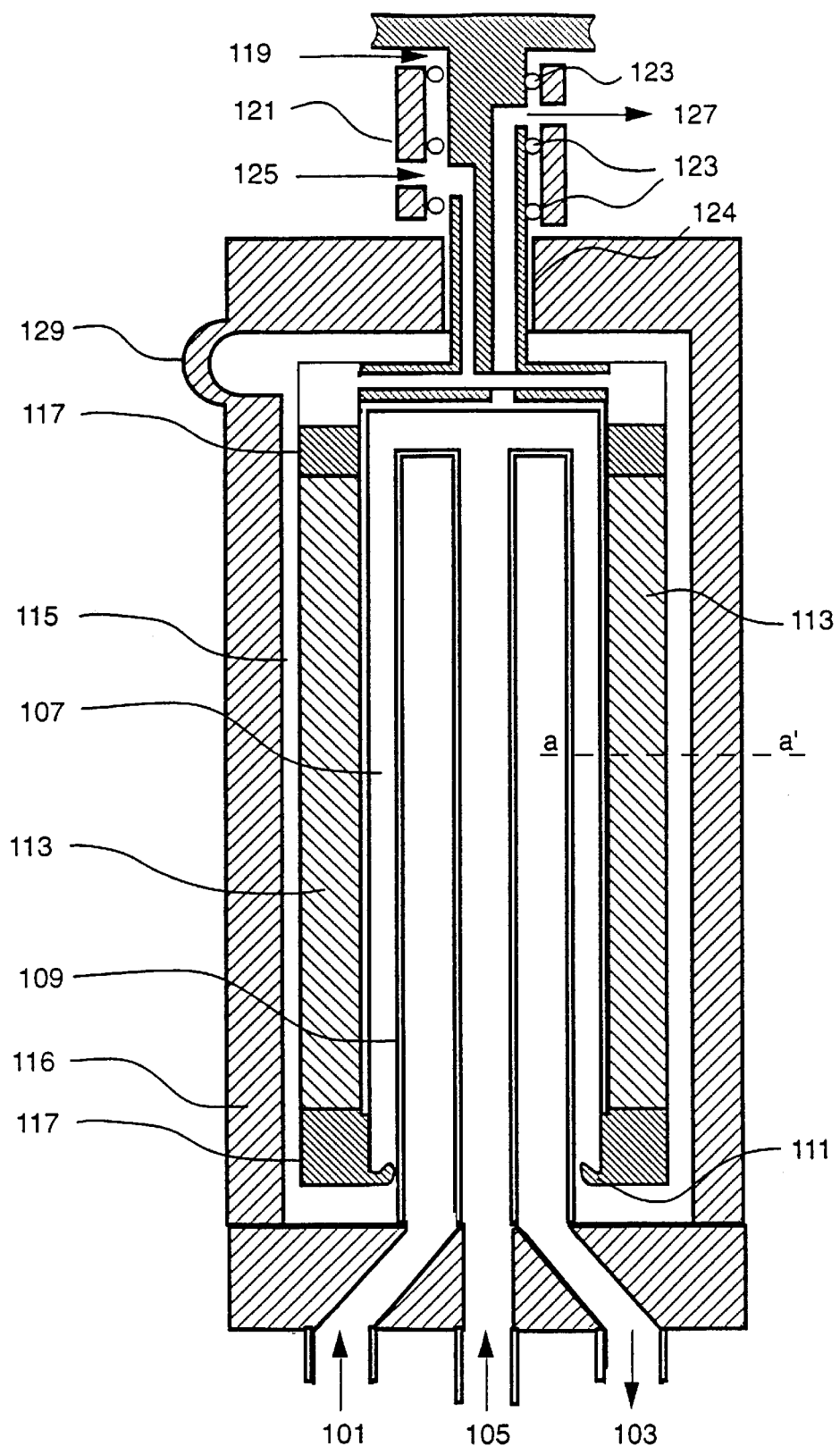
FIG. 3-A illustrates one working embodiment, in cross-section, in which the fiber bundle rotates between the central diffuser and outer shell and shear is applied to the boundary layer by the rotating action.

FIG. 3-A illustrates a working model of the principle illustrated in FIG. 2. Coolant enters at point 101 and exits at point 103 through ports in the central diffuser. Blood passes through channel 105 to inner blood space 107 where it is in contact with heat diffusion surface 109. The inner blood space 107 is constrained by lip seal 111 which forces blood to traverse the fiber bundle 113 to outer blood space 115, which is created between the fiber bundle 113 and the outer shell 116. The fiber bundle 113 is embedded in potting material 117 at each end. Rotor shaft 119 attached to a drive mechanism causes the cylindrical fiber bundle 113 to rotate in blood spaces 107 and 115. A stationary slip ring manifold 121 with appropriate seals 123 directs incoming gas 125 through the dual ducted shaft to the upper end of the fiber bundle 113. The rotor shaft 119 rotates within face seal 124 which prevents blood from leaking. Gas passes through the fibers, returns to the ducted shaft, and exits at the gas exhaust port 127. A pressure head generated by the Tesla effect propels blood through tangential exit 129.

FIG. 3-B is a magnified view, taken through plane a-a' in FIG. 3-A crossing heat exchange surface 109 of the central diffuser, blood path 107–115, fiber bundle 113, and shell 116. The putative levels of shear affecting the boundary layer at the surface of the fibers are shown. Shear is high as the blood enters (see arrows and notation at left of FIG. 3-B) into the central blood chamber 107 where the moving fibers oppose the stationary heat exchange surface 109. Shear decreases as the blood is accelerated to the speed of the fiber bundle in the central fiber bundle 113. Shear again increases as blood reaches the outer circumference of the fiber bundle which is in apposition to the stationary wall of the shell 116. Because of the greater radius of rotation, shear on the periphery of the bundle exceeds that on the interior of the bundle. FIG. 3-B illustrates the application of shear to the boundary layer by creating differential relative motion between the diffusing surface and the fluid in which the surface is immersed. It is believed that the highest shear and the greatest mass and thermal transfer occur where the greatest differential velocity exists for at least the following three reasons: (1) shear reduces the thickness of the boundary layer, thus reducing the impediment to diffusion across this relatively stationary fluid layer; (2) movement of mass away from the diffusing surface reduces the concentration thereat, increases the gradient in concentration across the membrane, and enhances diffusion through the thickness of the membrane; and (3) shear induces turbulence in the axial stream thus increasing transfer by conduction and convection.

A possible theoretical explanation for the foregoing follows in a greatly abbreviated form.

Fick's fundamental law of diffusion is first set out as follows:

$$dQ = -kS \frac{yc}{yx} dt \qquad \text{(Equation 1)}$$

where dQ=incremental volume of gas diffusing in the increment of time, dt; k=coefficient of diffusion which is specific for the particular gas and particular membrane expressed in units of area/unit time; S=area of membrane through which the gas diffuses; and yc/yx=the gradient of concentration of the gas (c) as a function of the thickness of the membrane (x). In Fitts, H. W. and Richards, D. W., *Respiratory System: External Respiration, in Medical Physics III,* Ed Glasser, O. Year Book Publishers, Chicago, 1960, Fitts and Richards review the following analytic solution to the behavior of an oxygen transporting membrane in capillaries with laminar flow (ignoring the boundary layer as being non-consequential as is currently conventional according to Kety quoted by Fitts and Richards, see also Kety, S. S. Pharmacol. Rev. 3:1, 1951):

$$dQ = -kS \left( \frac{C_1 - C_2}{x} \right) dt \qquad \text{(Equation 2)}$$

where $C_1-C_2$ expresses the differences in concentration of the gas. By substituting the Bunsen solubility coefficient (a) for the gas diffusing, and partial pressures for the respective concentrations, and combining k, S, a, x and 760 (ambient total pressure in the Bunsen coefficient) the expression can be simplified into a single term called diffusing capacity (D):

$$D = \frac{\left(\frac{dQ}{dt}\right)}{P_2 - P_1} \qquad \text{(Equation 3)}$$

Assuming that the rate of diffusion of oxygen is independent of absolute pressure, Equation 3 can be simplified to:

$$D_{O_2} = \frac{V_{O_2}}{P_{G_{O_2}} - P_{f_{O_2}}} \qquad \text{(Equation 4)}$$

where $V_{O_2}$=volume of $O_2$ diffusing per minute, $P_{G_{O_2}}$=tension of $O_2$ in the gas phase; and $P_{f_{O_2}}$=effective tension of $O_2$ in the fluid phase.

Typically, the diffusion capacity of an oxygenator can be described analytically provided: (a) the boundary layer is ignored; and (b) flow is laminar. As is shown by the performance data on this invention, the boundary layer cannot be ignored as is currently done in the analytic solutions of diffusion in capillary tubes. Moreover, it is unlikely that flow is laminar in the presence of the extreme levels of shear produced by the invention on the diffusing surface. Because the mathematical methods are not known by the inventors to exist for analogous analytic solution in turbulent flow, the following operational approximation of the invention is assumed:

the boundary layer consists of relatively static regime in which there exists successive layers of fluid, the partial pressure in which progress from that in the membrane phase to that in the axial stream of the blood phase. The boundary layer is then treated analytically as if it were a membrane behaving as in Equation 4. Assuming that the boundary layer, while relatively static, behaves like a membrane, the volume of oxygen diffusing is a direct function of the difference in partial pressures across the boundary layer (Equation 4).

FIG. 4 is a schematic postulate to explain the unique function on this basis. As indicated in FIG. 4-A, in the presence of laminar flow, a partial pressure gradient of 100 torr exists across the membrane, and a second gradient of 100 torr across the boundary layer are assumed to exist in the presence of a partial pressure of oxygen in the gas phase of 700 torr and in the incoming blood of 50 torr. As shear increases (FIG. 4-B), Tollmein-Schlichting waves (TS) destabilize and thin the boundary layer doubling the diffusion gradient across the boundary layer. This causes more rapid diffusion of gas away from the membrane and in turn doubles the gradient across the membrane, which further enhances diffusion. The theoretical result would be a doubling of diffusion across both the membrane and boundary layers as the gradient in partial pressure doubles across each ( $P_{G_{O_2}}- P_{f_{O_2}}$, see equation 4). As shear increases the critical Reynold's number in 4-B proceeds to full turbulence in 4-C. Turbulent transfer (heat and mass transfer, conduction and convection) is much greater than that provided by the molecular mechanism in laminar flow. Turbulence generates randomness and increases particle motion normal to the diffusing surface. This is schematically illustrated in FIG. 4-C where blood with a partial pressure of 50 torr comes into contact with the diffusing surface, further increasing the partial pressure gradient across the membrane and boundary layer.

The foregoing is merely an approximation for purposes of explanation. It ignores the classic analytic work of a number of investigators (e.g., Levich, V. G., *Physiochemical Hydrodynamics,* Prentice Hall, Englewood Cliffs, N.J., 1962 (English Translation from Russian) and Schlichting, H. *Boundary-Layer Theory,* McGraw Hill, New York 1978 (English translation from German)) who have attempted analytic solutions which approximate experimental data obtained in laminar and some turbulent regimes. However, the inventors know of no analytic work employing rotating microporous diffusing membranes, or mass transfer of any type through (in contrast to from) rotating surfaces. In Sherwood, T. K. Pigford, R. L., and Wilkie, C. R. *Mass Transfer,* McGraw Hill, New York 1975, the authors state on page 80:

"A plane circular disk is immersed in a fluid and caused to rotate at constant speed, with mass transfer occurring between the fluid and the surface of the disk ... would appear to have little application in engineering, but it is the basis for a very useful experimental technique for measurement of mass and heat transfer and is of use in electrochemistry."

It is experimentally useful in laminar flow. In turbulent flow, an exact solution of the Navier Stokes equation cannot be obtained. According to Owens, J. M. and Rogers, R. H., *Flow and Heat Transfer in Rotating Disk Systems, Vol. I. Motor-Stator Systems,* J. Wiley & Sons, New York, 1989, "[i]nside the boundary layer flow may be laminar or turbulent," depending on the Reynold's number locally on the surface. Levich has made estimates of the critical Reynold's number, but when the invention described herein is used with a non-Newtonian fluid such as blood, those estimates would not be expected to apply. A superimposed flow (flow in addition to that generated by the rotation of the disk surface) in the rotating disk system, further compounds attempts at analytic solution.

Suffice it to say that this process of the invention assumes particular importance for two reasons: First, Kety, preeminent authority on the analytical solution of capillary diffusion, found and indeed appears to recommend, that the boundary layer could be ignored. In contrast, the inventors herein suggest that when an aspect of the invention is used with microporous capillary tubes essentially all of the measurable impediment to diffusion resides in the boundary layer; second, Sherwood et. al., authorities on the rotating disk state, in contrast to performance of the invention, that there is little practical use for rotating disks in engineering.

Since our explanatory treatment of the boundary layer is hypothetical, and since mathematical methods do not currently exist for the analytic description of the invention, its function will be described by performance data determined experimentally in illustrative prototypes.

Figure 5:
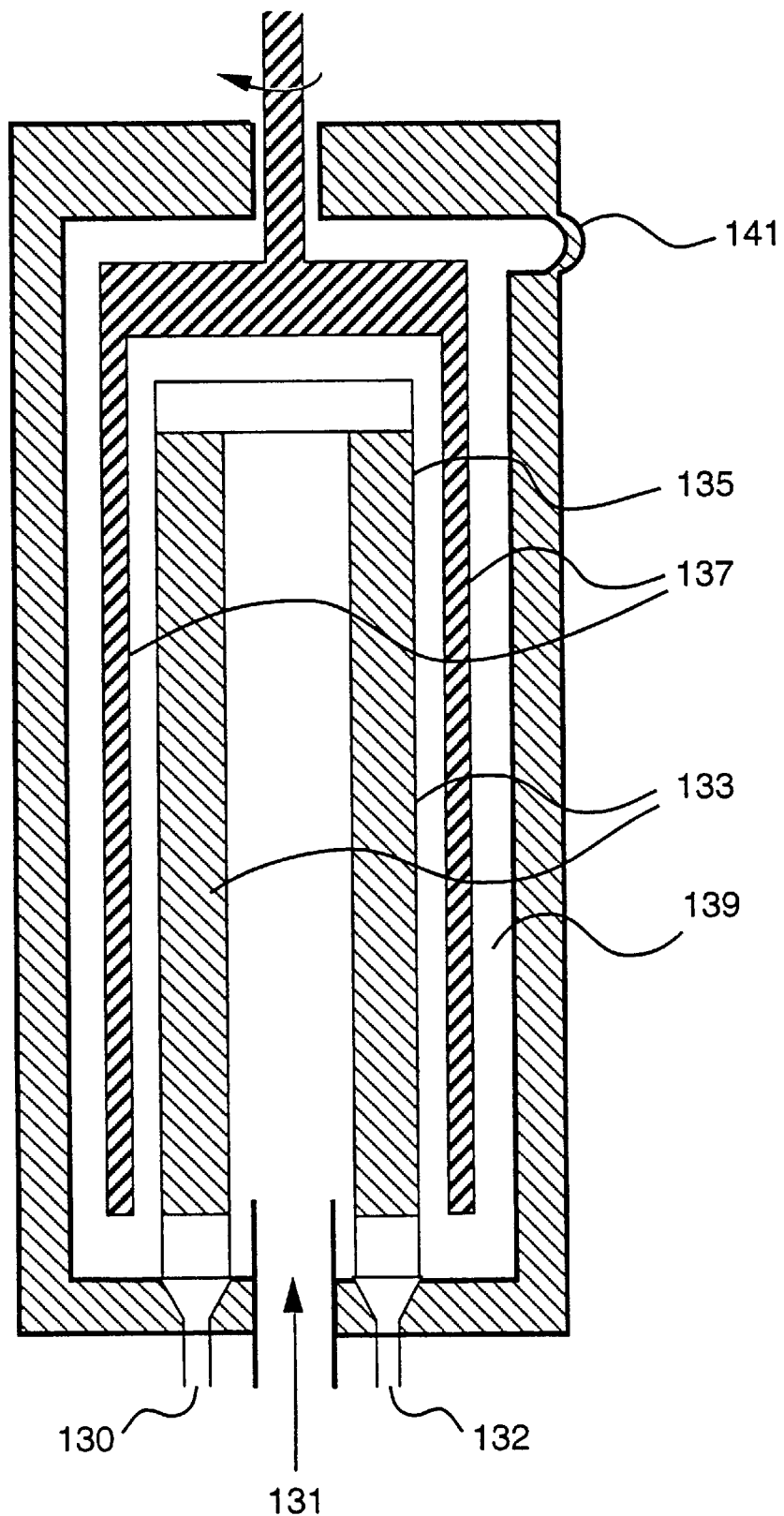
FIG. 5 shows another embodiment in which a rotating cylindrical member 137 creates a differential velocity and perturbs the boundary layer on the outer surface of the fiber bundle while the bundle remains stationary.
Figure 6:
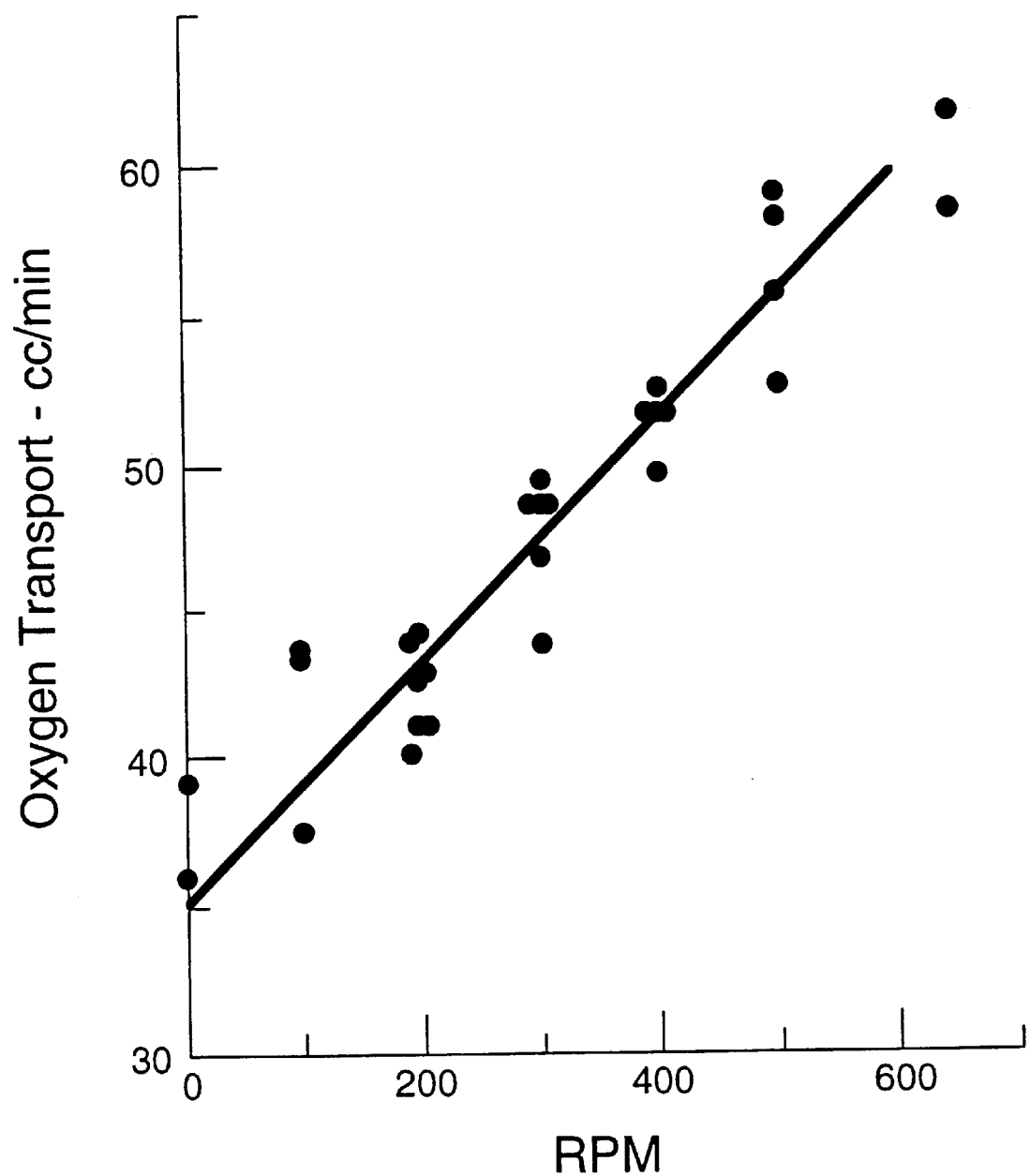
FIG. 6 is a graph showing the progressive increase in oxygen transport with increasing RPM in an embodiment employing 0.2 $M^2$ of membrane surface in a living animal.

Based on existing knowledge, it would be expected that a plot of the relationship between diffusion capacity and RPM of the claimed invention would produce a non-linear downward-concave asymptotic curve. The component of the diffusion barrier due to the membrane would remain constant while the component due to the boundary layer would progressively diminish with increasing RPM. This supposition is confirmed by the thermal transfer through a metallic surface exhibited by the prototype described below. Unexpectedly, the curve for gas transfer is absolutely linear to the highest RPM tested. We interpret this to mean that, contrary to generally accepted theory, the boundary layer is the principle embodiment to gaseous diffusion and that, at least in our device as tested, the diffusion barrier due to the microporous membrane is too small to be measured. This postulate may explain why investigators have found in the past that most thin membranes have (strangely) the same diffusion coefficient in the range of 70–150 cc/M$^2$/min. The graph in FIG. 6 shows the relationship between the rate of oxygen transport to the venous blood of a living animal and the rotation rate of the cylinder in an embodiment as represented in FIG. 5. There is an unexpected linear increase in oxygen transport with increasing RPM to the maximum RPM tested. The absolute mass of oxygen transported and the surface area of hollow fiber membrane used indicate that the invention has gas transport capability four- to six-fold greater than the best commercial oxygenators currently available. The curve may become asymptotic at some higher RPM when the boundary layer impediment is entirely removed and mass transfer is determined by the diffusion coefficient of the membrane itself. The linear relationship between RPM and oxygen transport suggests that the limit of the invention's ability to enhance transport has not yet been approached.

It is apparent that the same physical effects of shear on mass and thermal transfer apply whether the fiber bundle rotates in apposition to a fixed surface or when a surface rotates in apposition to a fixed fiber bundle. This makes feasible a number of alternative embodiments. Neither the foregoing nor any of the following embodiments represent a preferred form. Rather, each is illustrative of the principle of the invention from which numerous products may be developed.

Figure 8:
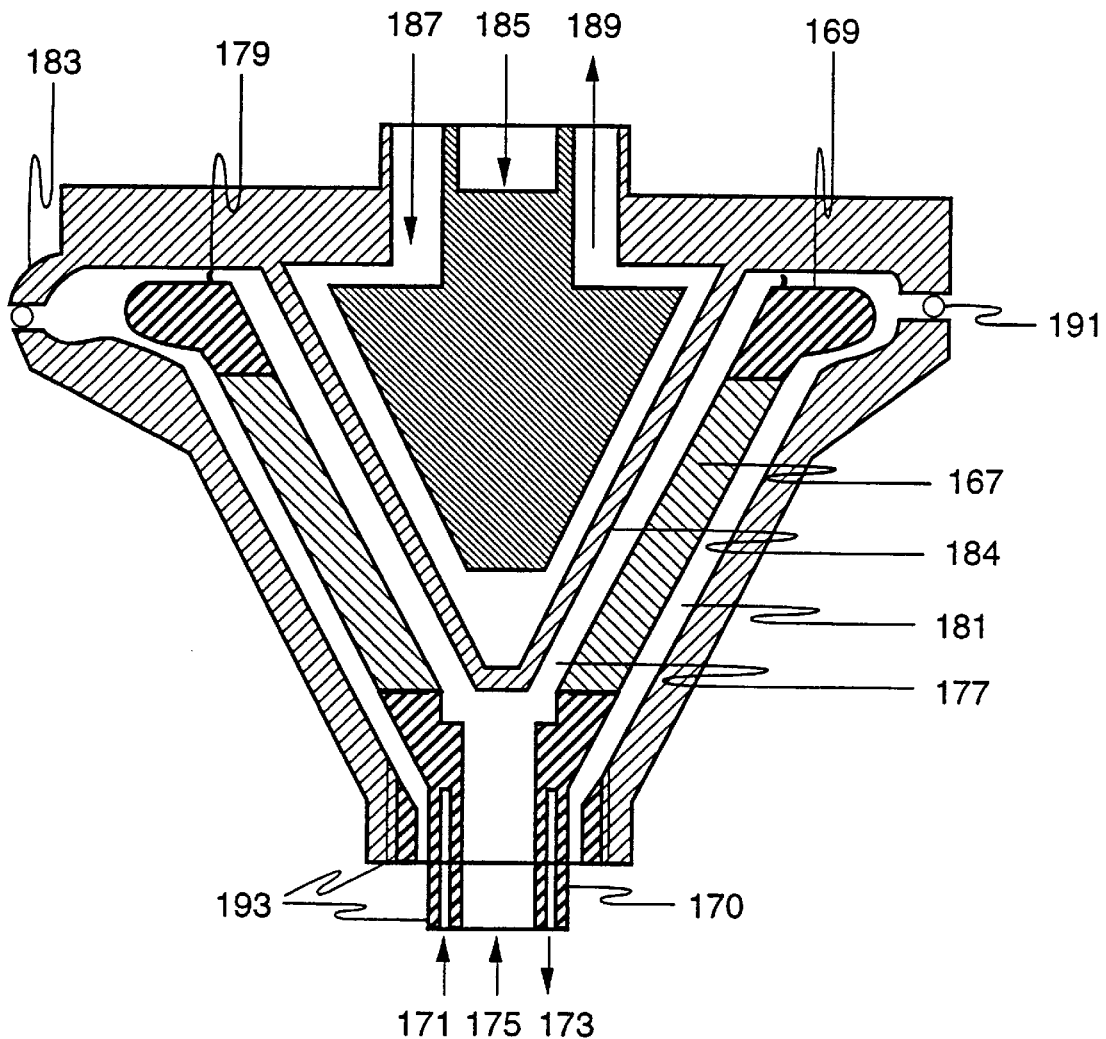
FIG. 8 is an embodiment, as illustrated in FIG. 1-B, in which the oxygenator, heat exchanger, pump and flow meter are combined in one unit and relative motion is achieved by a conical rotating fiber bundle 163 which also acts as a centrifugal pump to facilitate oxygenation and heat exchange and to achieve the other benefits discussed.
Figure 9:
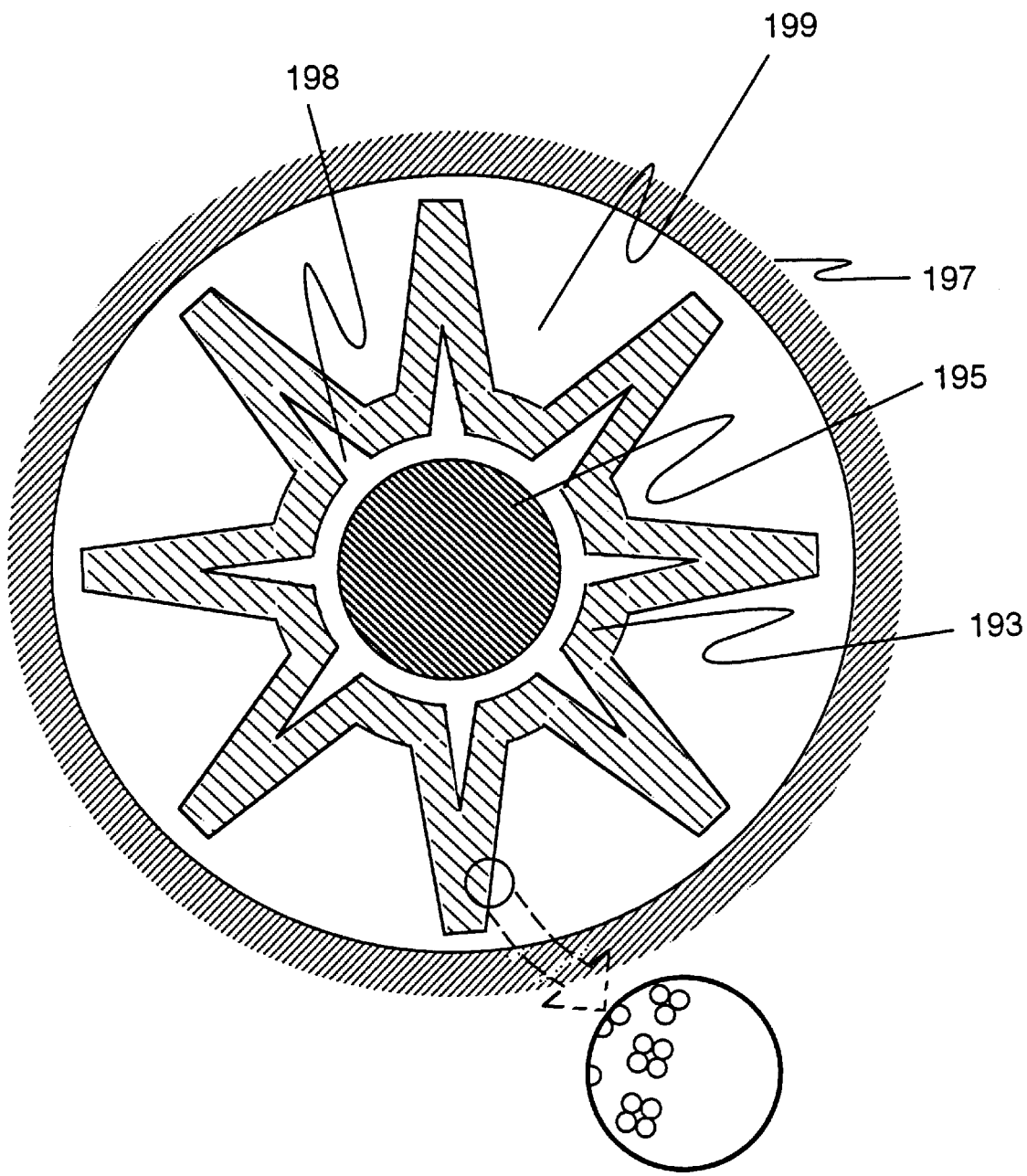
FIG. 9 is yet a different embodiment in which the hollow fibers are woven into a textile and crimped to create vanes which simultaneously oxygenate and pump blood as the fibers rotate.

FIG. 5 shows an alternative embodiment wherein the fiber bundle is stationary. Since it is relative (not absolute) motion of the hollow fibers which creates the differential velocity between fiber and blood, the prototype illustrated was designed with a stationary fiber bundle and a moving perturbing surface. Gas enters through port 130, travels within the hollow fibers of the hollow fiber bundle 133, and exits through port 132. Blood enters at port 131, passes through the stationary bundle 133, traverses inner blood space 135, and is subjected to shear on the outer surface of the bundle 133 by the rotating cylindrical member 137. The blood is accelerated in outer chamber 139 by the rotating cylinder 137 to develop a pressure head acting at blood exit 141. The heat exchanger and other details are not shown. As noted previously, FIG. 6 presents the function of this oxygenator in a living large animal. There is a progressive linear increase in the coefficient of oxygen transport with increasing RPM. In this embodiment, only the boundary layer on the outside of the hollow fiber bundle is subjected to shear, and transport would likely be further doubled if both sides of the bundle had been so treated as with the embodiment in FIG. 3-A. Because of the small radius of the rotating member, this conformation forms a relatively inefficient pump (Tesla type). Thus, the embodiments in the following FIGS. 7–9 are alternatives which further increase both gas transport and/or pumping efficiency.

Figure 7A:
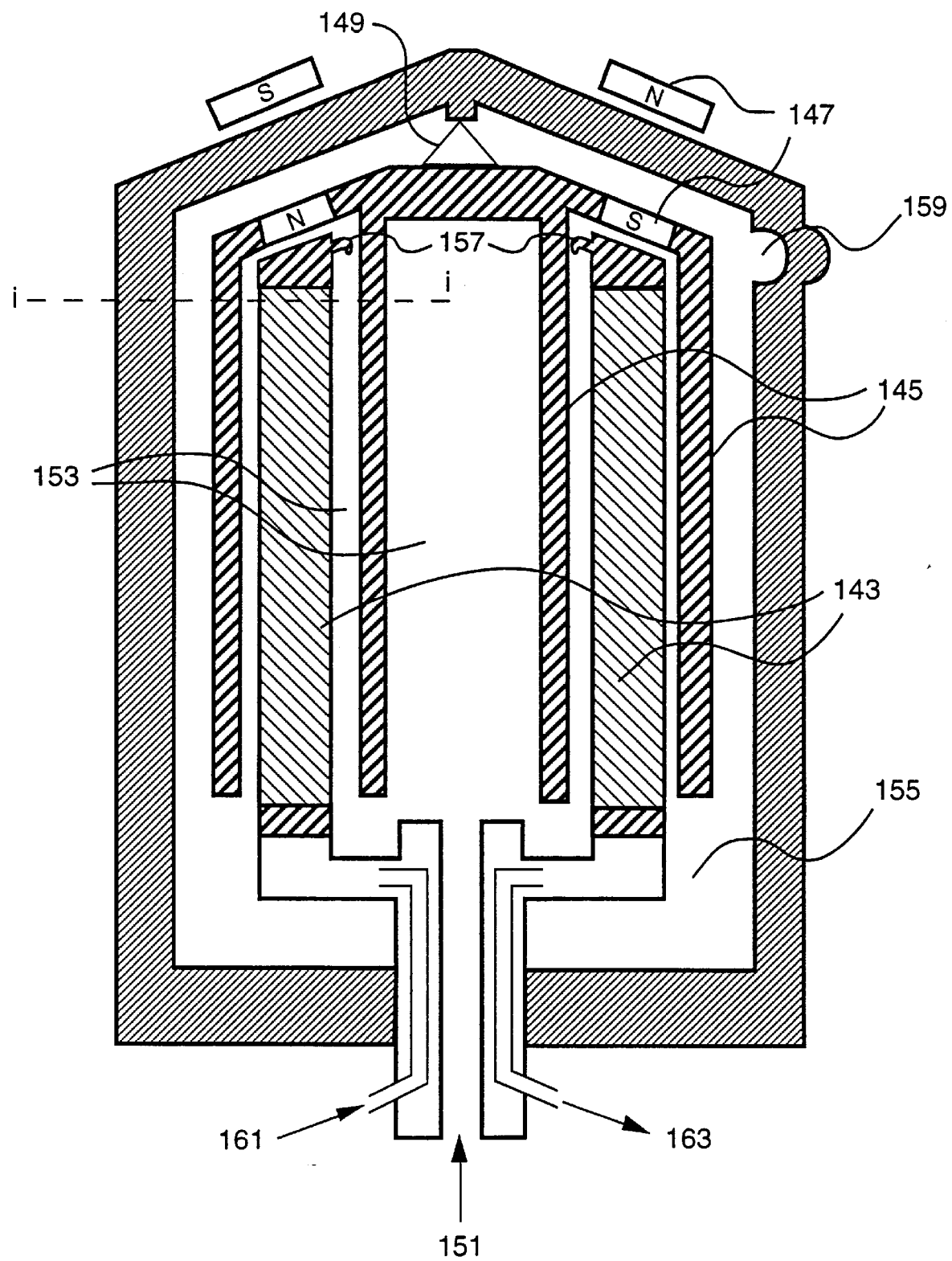
FIG. 7-A shows an embodiment in which dual rotating cylindrical member 145 perturbs the boundary layer on both sides of a stationary fiber bundle which would be expected to double the diffusion capacity of the embodiment in FIG. 6.

FIG. 7-A illustrates another embodiment employing a stationary fiber bundle 143 and rotating dual cylinders 145 driven and suspended by magnets 147 on jewelled bearing 149. Blood enters through path 151 into blood space 153 and passes through the stationary fiber bundle 143 to outer blood space 155. Lip seals 157 prevent the blood from flowing out of blood space 153 directly into blood space 155. Dual rotating cylinders 145 scrub both sides of the fiber bundle 143 and the outer cylinder generates the pressure head (Tesla) to propel blood through exit 159. Gas containing oxygen enters the fiber bundle via port 161 and exits via port 163.

Should the application of the invention require more efficient pumping, either for greater volume or greater pressure, the dual rotating cylinders in FIG. 7-A can be made more efficient by increasing the radius of rotation or adding vaned impellers as set out below in FIGS. 7-B through 7-E.

FIG. 7-B illustrates a modification of dual cylinder embodiment in FIG. 7-A designed to increase pumping efficiency. The cross section is taken through plane "i—i" in FIG. 7-A. Increased pumping efficiency is achieved by shortening the cylinder (s-s') and increasing the radius (r-r') as set out in FIG. 7-C. The same diffusing surface of hollow fibers 143 is retained in a configuration which generates a greater pressure head as the result of an increased radius of rotation.

FIG. 7-D illustrates yet another embodiment in which the inner cylindrical member 145 is retained as in the embodiments in FIGS. 7-A and 7-B, but the outer cylinder is replaced by vanes 165. These vanes not only perturb the boundary layer on the outer surface of the stationary fiber bundle 143, but they greatly improve pumping efficiency over that provided by the outer Tesla cylinder in FIGS. 7-A and 7-B. FIG. 7-E shows a schematic side view of the embodiment illustrated in FIG. 7-D.

FIG. 8 illustrates the embodiment in FIG. 1-B. Rotating fiber bundle 167 has an attached vaned impeller 169 to generate a propulsion head. The gas containing oxygen enters ducted shaft 170 via port 171, flows through the hollow fibers of the hollow fiber bundle 167, and exits through port 173. Blood enters ducted shaft 170 via port 175, flows into blood space 177 with lip seal 179, passes through rotating fiber bundle 167 into blood space 181 and is forced by vaned impeller 169 through exit port 183. The ducted shaft 170 is a modification of the manifolding in FIGS. 2 and 3. The heat exchange surface 184 is integral with the central diffuser 185 and is supplied with coolant via entry port 187 and exit port 189. The housing disassembles into two parts at "O" ring 191 so that after use, the fiber bundle, shaft, face seal and housing (all indicated as 193) may be discarded and replaced. Current surgical and hygienic practice requires discarding after each use $600 to $800 worth of equipment including an oxygenator and housing, heat exchanger and housing, and pump with bearings and housing. This embodiment offers the possibility of substantial savings in cost. Use of this embodiment for kidney dialysis employs wettable hollow fibers (cellophane derivative) with dialysate replacing the gas as discussed later.

Proceeding now to FIG. 9, the diffusing and pumping functions of the invention may be combined by weaving the hollow fibers 193 into a sheet of textile and then conforming it to a vane-type structure used to increase surface area. In this conformation, the fiber bundle 193 serves both as a diffusing surface and as the impeller of a centrifugal pump. The fluted fiber bundle 193 rotates between the central diffuser 195 and the outer shell 197. Blood is both oxygenated and propelled as it passes from inner blood space 198 to outer blood space 199.

Figure 10A:
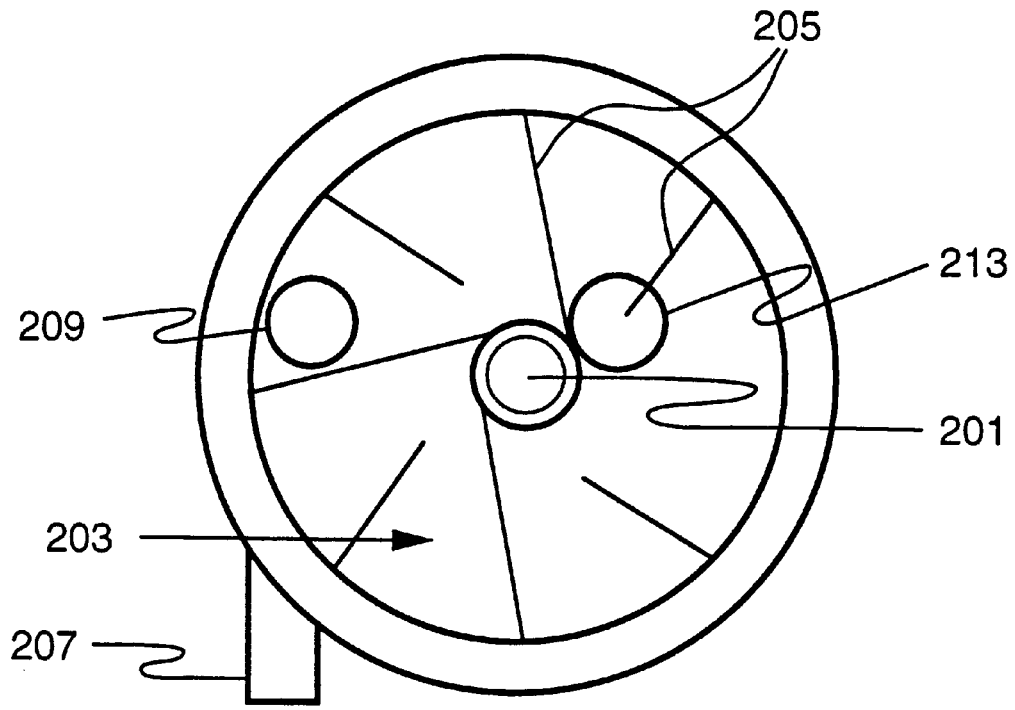
FIGS. 10-A and 10-B show a heat exchanger embodiment in which a conventional centrifugal blood pump is modified (shaded area) to act also as a heat exchanger by replacing half of the outer shell with a heat exchange surface.
Figure 10B:
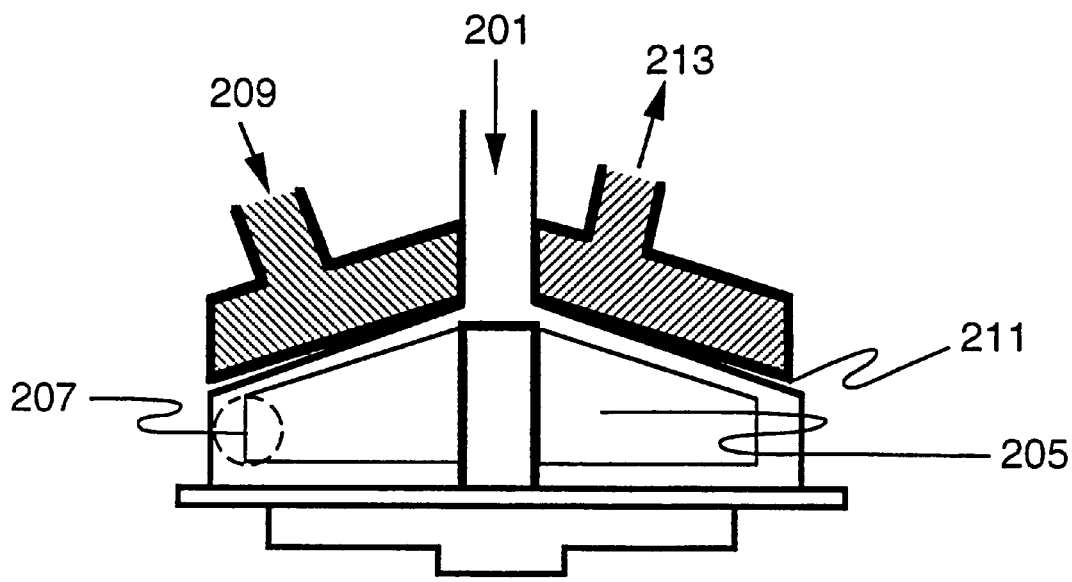
Figure 12:
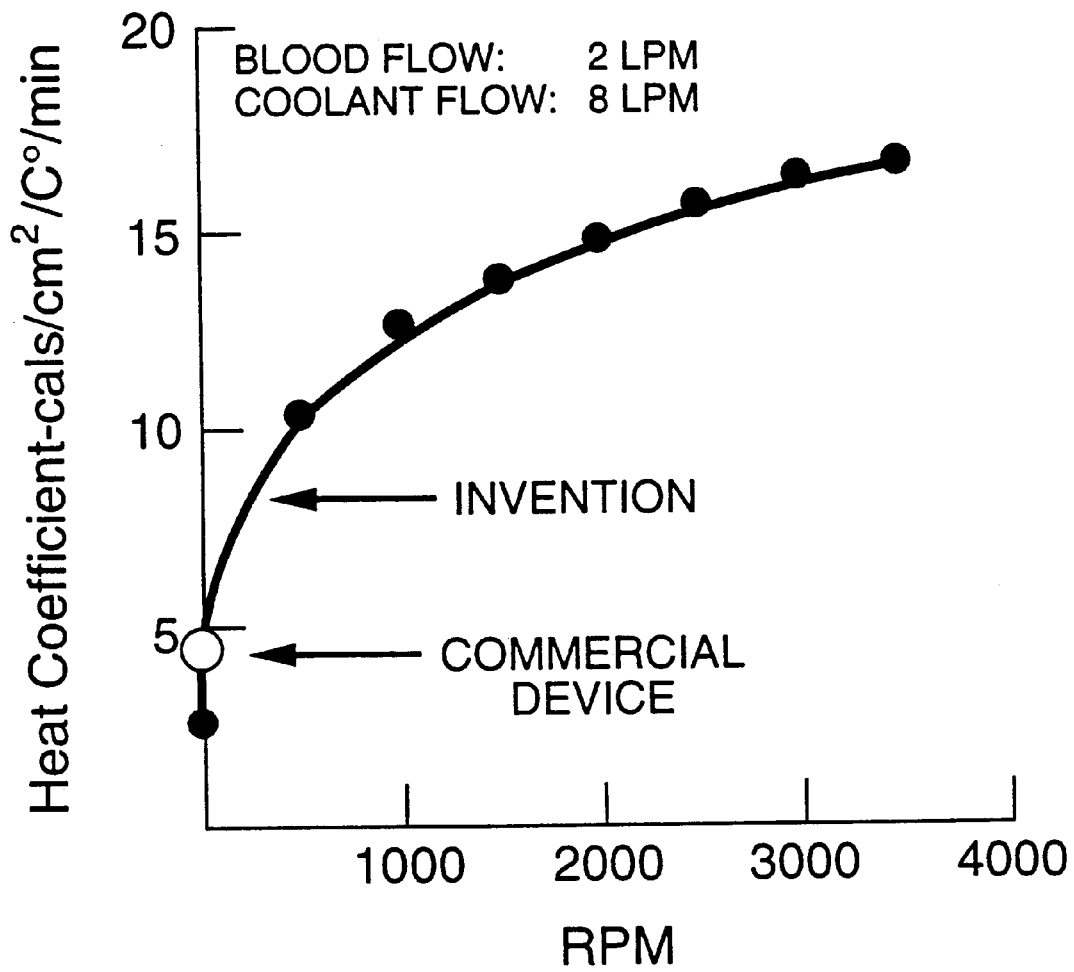
FIG. 12 illustrates how the principles disclosed herein can be used to improve blood heat exchangers. The heat coefficient of the combination pump and heat exchanger in FIGS. 10-A and 10-B progressively increases with RPM. Its performance is markedly superior to the known leading compact commercial blood heat exchanger.

The physical principle which enables the method of the invention to increase mass transport also provides analogous advantages in thermal transfer. FIGS. 10-A and 10-B show how a commercial vaned centrifugal blood pump (Centrimed/Sarnes) was modified by replacing one side of the pump housing with a conductive surface (43 cm$^2$) to convert it to a combination pump and heat exchanger. The shaded area in FIG. 10-B represents the modification. Blood enters the centrifugal pump via port 201 into the blood space 203 between the rotating vanes 205. The rotating vanes 205 generate a centrifugal force that causes the blood to exit the centrifugal pump via port 207. Coolant flows from entry port 209, across the heat exchange surface 211, and exits via port 213. Since the heat exchange surface 211 is integral with the device, there is no priming volume required as compared to the typical volumes of 75 ml to 150 ml in commercial exchangers. The overall component size determined by coolant volume with the invention is one-tenth that of state-of-the-art heat exchangers. The graph in FIG. 12 illustrates the progressive rise in the coefficient of thermal transfer with RPM. The performance of the prototype exceeds the leading compact commercial blood heat exchanger at identical coolant and blood flow rates in the physiologic temperature range. The coefficient of heat transfer (cals/cm$^2$/C.°/min) was 3.5 times greater for the invention than that for the leading commercial device at 3,500 RPM.

Figure 11:
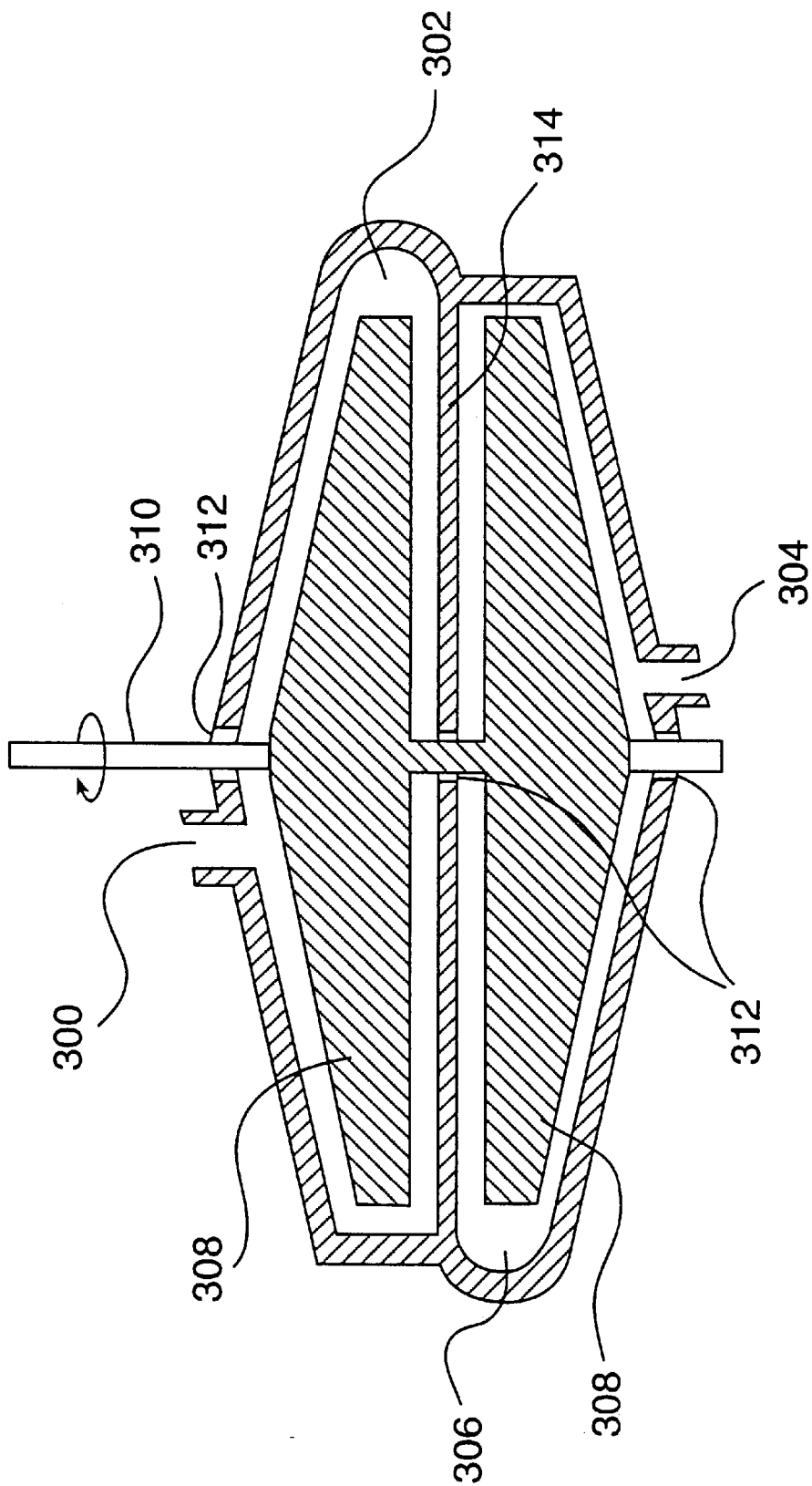
FIG. 11 is a pictorial representation of a centrifugal heat exchanger utilizing two rotating members to perturb the boundary layer in two fluids, one of which is a coolant; moreover, each fluid is pumped in the desired direction.

Turning to FIG. 11, a further improvement in thermal exchange is illustrated. The capacity to perturb the boundary layer on both sides of the diffusing surface combined with dual chamber pumping capacity is presented. Blood enters port 300 and is propelled by rotating vanes 308 to exit through tangential exit 302. Coolant follows an analogous path through port 304, past vanes 308, to exit 306. The rotating vanes 308 are attached to rotating shaft 310. Seals 312 are used to keep the fluid from leaking out of the chambers down the rotating shaft 310.

FIGS. 10-A, 10-B, 11, and 12 represent embodiments of one of the aspects of the claimed invention common to most or all embodiments. However, in the instances illustrated, the perturbation of the diffusing surface for heat exchange is accomplished in association with pumping without the simultaneous enhancement of mass transfers (e.g. oxygenation). In FIGS. 10-A and 10-B, pumping with enhancement of heat exchange on one side of the diffusion surface is accomplished. In FIG. 11, perturbation of the boundary layer and enhancement of thermal exchange occurs on both sides of the diffusion surface, in combination with dual chamber pumping.

These two embodiments, together with those presented in conjunction with mass transport of oxygen, illustrate the flexibility available in the application of the method of one aspect of the invention depending on the user's objectives. It is possible to use singly or in various combinations the following functions: mass transport (gasses, liquids, molecules, and solvents); thermal exchange; pumping (single or double chambers); and flow measurement.

Although hundreds of individuals and a score of companies skilled in the art of extracorporeal circulation and dialysis manufacture and sell millions of pumps (both vaned and Tesla types), heat exchangers, and dialyzers, to the inventors' knowledge, none have conceived the possibility of the claimed invention. Theoreticians, working in the field of chemical engineering with mass transfer on rotating disks have even specifically stated that they see no practical application for rotating disks.

Apart from medical applications, the process of the invention should have application in industry. For example, the heat exchangers used in marine diesel engines typically separate salt and fresh cooling water with a tube and shell exchanger measuring 6×6×20 inches. If the thermoconductive bundle of tubes were rotated inside the shell casing by the same shaft that drives the water pump, the exchanger should be able to be reduced to about 15% of its current size. Although priming volume is not of concern in this application, reduction of engine size is beneficial.

Turning now to FIG. 13, the integral flow meter aspect of the invention is shown. FIG. 13 is a three-dimensional diagram of the relationship between RPM, flow and pressure head in a shear-type centrifugal pump (e.g., FIG. 7-A). Since knowledge of the RPM is essential to operation of the device and is therefore available, a simple measure of the differential pressure between blood entrance and exit provides a continuous indication of flow. The economy compared to the common Doppler or electromagnetic flow meters is great.

The same principles described in the above embodiments can be applied to artificial kidneys. The essence of the artificial kidney is a wettable membrane (typically a cellophane derivative) which separates blood from the patient from a large reservoir of dialysis solution. The direction and velocity of mass transfer of molecular species between the two fluids is determined by the concentration gradient and diffusion coefficient of each species across the membrane. The mass transfer of free water is influenced by any differential pressure across the membrane (ultrafiltration), and by the difference in oncotic pressure of non-diffusible molecular species such as large protein molecules. In use, the composition of the dialysate is adjusted to retain desired components in the blood and cause undesired components such as creatinine and potassium to diffuse with the dialysate. The duration of the four hour dialysis treatments is determined by the diffusion capacity of the artificial membrane and by diffusion coefficients of cellular membranes within the body. The invention will directly benefit the former and will indirectly benefit the latter by decreasing the concentration of undesired components returning to the body from the dialyzer.

While multiple embodiments and applications of this invention have been shown and described, it should be apparent that many more modifications are possible without departing from the inventive concepts therein. Both product and process claims have been included and it is understood that the substance of some of the claims can vary and still be within the scope of this invention. The invention therefore, can be expanded and is not to be restricted except as defined in the appended claims and reasonable equivalence departing therefrom.

What is claimed is:

1. A combined oxygenator and pump comprising:
   (a) a container for holding blood having an inlet and an outlet;
   (b) a substantially cylindrical central diffuser for introducing blood into said container;
   (c) a rotatable bundle of non-wettable microporous hollow tubes concentrically positioned around and outside said central diffuser;
   (d) means for rotating said bundle around said central diffuser;
   (e) means for introducing oxygen into said hollow tubes in said bundle; and
   (f) whereby the rotation of said bundle causes a differential pressure head across said container resulting in desired pumping of said blood through said container and improved diffusion of oxygen into said blood by creating turbulent flow.

2. A combined oxygenator and pump as claimed in claim 1, whereby said oxygenator and pump also contain a heat exchanging means for controlling the temperature of the blood comprising the use of the inherent shear forces created by said rotation of said fiber bundle to enhance thermal transfer.

3. A blood oxygenator comprising:
   (a) a housing;
   (b) non-wettable hollow tubes that are bundled together separating two fluids located within said housing;
   (c) one of the two said fluids being blood;
   (d) the other said fluid contains some oxygen; and
   (e) means for perturbing the boundary layer to produce turbulence in said blood adjacent to said hollow tubes by rotating said bundle of hollow tubes.

4. The apparatus of claim 3 wherein said hollow tube bundle is connected to at least one vaned impeller.

5. The apparatus of claim 4 wherein the hollow tube bundle is conically shaped.

6. The apparatus of claim 4 wherein the hollow tube bundle is cylindrically shaped.

7. The apparatus of claim 3 wherein the apparatus is connected to a non-dynamic or dynamic blood reservoir.

8. The apparatus of claim 3 wherein the rotational movement of said hollow tubes is used to pump blood.

9. The apparatus of claim 3 also including a means for heat exchange.

10. The apparatus of claim 9 wherein the boundary layer of the surface of said heat exchanger is perturbed by the rotary motion of said hollow tubes.

11. The apparatus of claim 5 also including within the oxygenator a central diffuser for the introduction of blood.

12. The apparatus of claim 11 wherein said central diffuser contains at least two separate compartments, one for introducing blood, and the other for introducing coolant to accomplish heat exchange.

13. A blood oxygenator comprising:
   (a) a housing;
   (b) a stationary bundle of non-wettable hollow tubes wherein said hollow tubes separate two fluids located within said housing;
   (c) one of two said fluids being blood;
   (d) the other said fluid contains some oxygen; and
   (e) means for perturbing the boundary layer to produce turbulence by the Tesla shear principle in said blood adjacent to said hollow tubes by rotating one or more cylindrical walls in apposition to said stationary bundle of hollow tubes.

14. The apparatus of claim 13 wherein said hollow tube bundle is cylindrically shaped.

15. The apparatus of claim 13 wherein in said hollow tube bundle is conically shaped.

16. The apparatus of claim 13 wherein the apparatus in connected to a non-dynamic or dynamic blood reservoir.

17. The apparatus of claim 13 wherein the rotational movement of said rotatable member is used to pump blood.

18. The apparatus of claim 13 also including a means for heat exchange.

19. The apparatus of claim 18 wherein the boundary layer of the surface on the heat exchanger is perturbed by the rotary motion of one or more of said rotating cylindrical walls.

20. The apparatus of claim 13 also including within the oxygenator a central diffuser for the introduction of blood.

21. The apparatus of claim 20 wherein the central diffuser contains at least two separate compartments, one for introducing blood, and the other for introducing coolant to accomplish heat exchange.

22. The apparatus of claim 13 wherein said rotating cylindrical walls are rotated by driven stationary magnets affixed to said rotating cylindrical walls and driving rotating magnets attached to a rotating armature adjacent thereto so that rotating movement of the driving magnets causes rotation of the driven magnets which in turn cause said rotating cylindrical walls to rotate.

23. The apparatus of claim 13 wherein a jeweled bearing is used for rotation of said cylindrical walls.

24. The apparatus of claim 13 wherein said rotating cylindrical walls comprises an armature driven by a power rotatable drive shaft.

25. The oxygenator of claim 13 wherein said rotatable walls are located inside and outside said fiber bundle.

26. A method of oxygenating blood comprised of the following steps:

(a) causing blood to flow into a reservoir;

(b) placing hollow microporous tubes made up of non-wettable diffusing material in said reservoir;

(c) causing a gas containing some oxygen to flow inside said hollow microporous tubes; and (d) rotating said hollow microporous tubes around an axis in said reservoir;

whereby turbulent perturbation of the boundary layer between the outer diffusing surface and the blood is at least caused to occur.

* * * * *